US008338426B2

(12) United States Patent
Dvorak et al.

(10) Patent No.: US 8,338,426 B2
(45) Date of Patent: Dec. 25, 2012

(54) PIPERAZINYL DERIVATIVES USEFUL AS MODULATORS OF THE NEUROPEPTIDE Y$_2$ RECEPTOR

(75) Inventors: Curt A. Dvorak, Poway, CA (US);
Devin M. Swanson, La Jolla, CA (US);
Victoria D. Wong, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 229 days.

(21) Appl. No.: 12/667,578

(22) PCT Filed: Jun. 26, 2008

(86) PCT No.: PCT/US2008/068289
§ 371 (c)(1),
(2), (4) Date: Jan. 4, 2010

(87) PCT Pub. No.: WO2009/006185
PCT Pub. Date: Jan. 8, 2009

(65) Prior Publication Data
US 2011/0046151 A1    Feb. 24, 2011

Related U.S. Application Data

(60) Provisional application No. 60/947,758, filed on Jul. 3, 2007.

(51) Int. Cl.
*A61K 31/496* (2006.01)
*C07D 213/56* (2006.01)
(52) U.S. Cl. .................. 514/253.01; 544/360
(58) Field of Classification Search ............... None
See application file for complete search history.

(56) References Cited

U.S. PATENT DOCUMENTS

| | | | |
|---|---|---|---|
| 5,177,087 A | 1/1993 | Goto et al. | |
| 6,906,073 B2 | 6/2005 | Du Bois et al. | |

FOREIGN PATENT DOCUMENTS

| | | |
|---|---|---|
| CA | 2007553 A1 | 7/1990 |
| WO | WO 01 92241 A1 | 12/2001 |
| WO | WO 02 20501 A2 | 3/2002 |
| WO | WO 02 42271 A2 | 5/2002 |
| WO | WO 2007 053436 A1 | 5/2007 |

OTHER PUBLICATIONS

Baldock et al "Hypothalamic Y2 Receptors Regulate Bone Formation" Clin Invest 2002 vol. 109 pp. 915-921.
Batterham et al "Gut Hormone PYY3-36 Physiologically Inhibits Food Intake" Nature 2002 vol. 418 pp. 650-654.
Bonaventure et al "Characterization of N-1(1-Acetyl-2,3-Dihydro-1H-Indol-6-Yl)-3-(3-Cyano-Phenyl)-N-[1-(2-Cyclopentyl-Ethyl)-Piperidin-4Yl]Acrylamide (JNJ-5207787), A Small Molecule Antagonist of the Neuropeptide Y Y2 Receptor" J Pharmacol Exp Ther 2004 vol. 308 pp. 1130-1137.
Castan et al "Identification and Functional Studies of a Specific Peptide YY-Preferring Receptor in Dog Adipocytes" Endocrinology 1992 vol. 131 pp. 1970-1976.
Clark et al "Neuropeptide y and Human Pancreatic Polypeptide Stimulate Feeding Behavior in Rats" Endocrinolgy 1984 vol. 115 pp. 427-429.
Dautzenberg et al "Stimulation of Neuropeptide-Y Mediated Calcium Responses in Human SMS-KAN Neuroblastoma Cells Endogenously Expressing Y2 Receptors by Co-Expression of Chimeric G Proteins" Biochemical Pharmacology 2005 vol. 69 pp. 1493-1499.
Dodds et al "BIIE0246: A Selective and High Affinity Neuropeptide Y Y2 Receptor Antagonist" Eur J Pharmacol 1999 vol. 384 pp. R3-R5.
Flood et al Modulation of Memory Processing by Neuropeptide Y: Brain Res 1987 vol. 421 pp. 280-290.
Fuhlendorff et al "[LEU31, PRO34] Neuropeptide Y: Specific Y1 Receptor Agonist" Proc Natl Acad Sci USA 1990 vol. 87 pp. 182-186.
Gehlert et al "Neuropeptide Y Antagonists: Clinical Promise and Recent Developments" Curr Pharm Des 1995 vol. 1 pp. 295-304.
Gerald et al "A Receptor Subtype Involved in Neuropeptide Y Induced Food Intake" Nature 1996 vol. 382 pp. 168-171.
Grouzman et al "Characterization of a Selective Antagonist of Neuropeptide Y At the Y2 Receptor"J. Biol Chem 1997 vol. 272 pp. 7699-7706.
Grundemar et al "Neuropeptide Y Acts at an Atypical Receptor to Evoke Cardiovascular Depression and to Inhibit Glutamate Responsivness in Brainstem"J Pharmacol Exp Ther 1991 vol. 258 pp. 633-638.
Heilig et al "Centraly Administered Neuropeptide Y (NPY) Produces Anxiolytic-Like Effects in Animal Anxiety Models" Physchopharmacology 1989 vol. 98 pp. 524-529.
Heilig et al "Anxiolytic-Like Effect of Neuropeptide Y (NPY), But Not Other Peptides in an Operant Conflict Test" Regul Pept 1992 vol. 41 pp. 61-69.
Heilig et al "Anxiolytic-Like Action of Neuropeptide Y: Mediation by Y1 Receptor in Amygdala, and Dissociation From Food Intake Effects" Neuropsychopharmacology 1993 vol. 8 pp. 357-363.
Heilig et al "Antidepressant Drugs Increase the Concentration of Neuropeptide Y (NPY)-Like Immunoreactivity in the Rat Brain" Eur J Pharmacol 1988 vol. 147 pp. 465-467.
Herzog et al "Hypothalamic Y2 Receptors: Central Coordination of Energy Homeostatis and Bone Mass Regulation" Drug News & Perspectives 2002 vol. 15 pp. 506-510.
Kalra et al "Neuropeptide Y: A Novel Neuroendocrine Peptide in the Control of Pituitary Hormone Secretion, and Its Relation to Luteinizing Hormone" Front Neuroendocrinol 1992 vol. 13 pp. 1-46.
Laburthe et al "Interaction of Peptide YY With Rat Intestinal Epithelial Plasma Membranes: Binding of the Radioiodinated Peptide" Endocrinology 1986 vol. 118 pp. 1910-1917.
Larhammar et al "Cloning and Functional Expression of a Human Neuropeptide Y/Peptide YY Receptor of the Y1 Type" J Biol Chem 1992 vol. 267 pp. 10935-10938.
Levine et al "Neuropeptide Y: A Potent Inducer of Consummatory Behavior in Rats" Peptides 1984 vol. 5 pp. 1025-1029.

(Continued)

*Primary Examiner* — Emily Bernhardt
(74) *Attorney, Agent, or Firm* — Samuel M. Kais

(57) ABSTRACT

The present invention is directed to piperazinyl derivatives useful as inhibitors of the NPY Y2 receptor, pharmaceutical compositions comprising said compounds, processes for the preparation of said compounds and the use of said compounds for the treatment and/or prevention of disorders, diseases and conditions mediated by the NPY Y2 receptor.

15 Claims, 5 Drawing Sheets

OTHER PUBLICATIONS

Lundberg et al "Recent Development With Neuropeptide Y Receptor Antagonists" Trends Pharmacol Sci 1996 vol. 17 pp. 301-303.

Morris et al "Increases in Plasma Neuropeptide Y Concentrations During Sympathetic Activation in Man" J Auton Nerv Syst 1986 vol. 17 pp. 143-149.

Stanley et al "Neuropeptide Y: Stimulation of Feeding and Drinking by Injection Into the Paraventricular Nucleus" Life Sci 1984 vol. 35 pp. 2635-2642.

Stanley et al "Neuropeptide Y Injected in the Paraventricular Hypothalamus: A Powerful Stimulatn of Feeding Behavior" Proc Nat Acad Sci USA 1985 vol. 82 pp. 3940-3943.

Tatemoto et al "Neuropeptide Y—A Novel Brain Peptide With Structural Similarities to Peptide YY and Pancreatic Polypeptide" Nature 1982 vol. 296 pp. 659-660.

Thiele et al "A Role for Neuropeptide Y in Neurobiological Responses to Ethanol and Drugs of Abuse" Neuropeptides 2004 vol. 38(4) pp. 235-243.

Thiele et al "Assessment of Ethanol Consumption and Water Drinking by NPY Y2 Receptor Knockout Mice" Peptides 2004 vol. 25(6) pp. 975-983.

Wahlestedt et al "Neuropeptide Y Receptor Subtypes Y1 and Y2" Ann N.Y. Acad Sci 1990 vol. 611 pp. 7-26.

Wahlestedt et al Evidence for Different Pre- and Post-Junctional Receptors for Neuropeptide Y and Related Peptides Regul Pept 1986 vol. 13 pp. 307-318.

Wetterau et al "Purification and Characterization of Microsomal Triglyceride and Cholesterol Ester Transfer Protein From Bovine Liver Microsomes" Chemistry and Physics of Lipids 1985 vol. 38 pp. 205-222.

Weinberg et al "Cloning and Expression of a Novel Neuropeptide Y Receptor" J Biol Chem 1996 vol. 271 pp. 16435-1638.

Widdowson et al "Reduced Neuropeptide Y Concentrations in Suicide Brain" J Neurochem 1992 vol. 59 pp. 73-80.

Time dependency of ex vivo $Y_2$ receptor occupancy in rat hippocampus following SC administration of the compound of formula (A) at 10 mg/kg, n = 3 (filled triangles); Corresponding rat plasma concentrations for the compound of formula (A) after SC administration at 10 mg/kg, n = 3 (open squares)

Dose dependency on ex vivo $Y_2$ receptor occupancy in rat hippocampus, following SC administration (at t = 60 min, n = 3) of the compound of formula (A)

Pharmacokinetics for the compound of formula (A) following oral (5 mg/kg, filled circle) and intravenous (0.5 mg/kg, open triangle) administration in the male beagle dogs.

Effects of the compound of formula (A) (10 mg/kg, i.p.) on ethanol (1g/kg, i.p.)-induced hyperactivity.

Effects of the compound of formula (A) (dosing at 1, 3 and 10 mg/kg, i.p., n=5-7/group) on amphetamine (3 mg/kg, s.c.) induced hyperactivity.

PIPERAZINYL DERIVATIVES USEFUL AS MODULATORS OF THE NEUROPEPTIDE $Y_2$ RECEPTOR

CROSS-REFERENCE TO RELATED APPLICATIONS

This application is a national phase of International Application No. PCT/US2008/068289 filed on Jun. 26, 2008 and claims benefit of priority under 35 U.S.C. §119(e) of U.S. Provisional Application No. 60/947,758 filed on Jul. 3, 2007.

FIELD OF THE INVENTION

The present invention is directed to piperazinyl derivatives useful as inhibitors of the NPY $Y_2$ receptor, pharmaceutical compositions comprising said compounds, processes for the preparation of said compounds and the use of said compounds for the treatment and/or prevention of disorders, diseases and conditions mediated by the NPY $Y_2$ receptor, including, but not limited to anxiolytic disorders, depression; pain, injured mammalian nerve tissue; conditions responsive to treatment with a neurotrophic factor; neurological disorders; bone loss; cardiovascular diseases; sleep-wake state disorders, substance abuse and addiction related disorders; obesity; and obesity-related disorders. The compounds of the present invention are further useful in modulating endocrine functions; particularly endocrine functions controlled by the pituitary and hypothalamic glands, and are therefore useful in the treatment of metabolic disorders, inovulation and infertility.

BACKGROUND OF THE INVENTION

Regulation and function of the mammalian central nervous system is governed by a series of interdependent receptors, neurons, neurotransmitters, and proteins. The neurons play a vital role in this system, for when externally or internally stimulated, they react by releasing neurotransmitters that bind to specific proteins. Common examples of endogenous small molecule neurotransmitters such as acetylcholine, adrenaline, norepinephrine, dopamine, serotonin, glutamate, and gamma-aminobutyric acid are well known, as are the specific receptors that recognize these compounds as ligands ("The Biochemical Basis of Neuropharmacology", Sixth Edition, Cooper, J. R.; Bloom, F. E.; Roth, R. H. Eds., Oxford University Press, New York, N.Y. 1991).

In addition to the endogenous small molecule neurotransmitters, there is increasing evidence that neuropeptides play an integral role in neuronal operations. Neuropeptides are now believed to be co-localized with perhaps more than one-half of the 100 billion neurons of the human central nervous system. In addition to being found in humans, neuropeptides have been discovered in a number of animal species. In some instances, the composition of these peptides is remarkably homogenous among species. This finding suggests that the function of neuropeptides is vital and has been impervious to evolutionary changes. Furthermore, neuropeptides, unlike small molecule neurotransmitters, are typically synthesized by the neuronal ribosome. In some cases, the active neuropeptides are produced as part of a larger protein that is enzymatically processed to yield the active substance. Based upon these differences, compared to small molecule neurotransmitters, neuropeptide-based strategies may offer novel therapies for the treatment of CNS diseases and disorders. Specifically, agents that affect the binding of neuropeptides to their respective receptors or that ameliorate responses that are mediated by neuropeptides are potential therapies for diseases associated with neuropeptides.

There are a number of afflictions that are associated with the complex interdependent system of receptors and ligands within the central nervous system; these include neurodegenerative diseases, affective disorders such as anxiety, depression, pain and schizophrenia, and affective conditions that include a metabolic component, namely obesity. Such conditions, disorders, and diseases have been treated with small molecules and peptides that modulate neuronal responses to endogenous neurotransmitters.

One example of this class of neuropeptides is neuropeptide Y (NPY). NPY was first isolated from porcine brain (Tatemoto, K. et al. Nature 1982, 296, 659) and was shown to be structurally similar to other members of the pancreatic polypeptide (PP) family such as peptide YY (PYY), which is primarily synthesized by endocrine cells in the gut, and pancreatic polypeptide, which is synthesized by the pancreas. NPY is a single peptide protein that consists of thirty-six amino acids containing an amidated C-terminus. Like other members of the pancreatic polypeptide family, NPY has a distinctive conformation that consists of an N-terminal polyproline helical region and an amphiphilic alpha-helix joined by a characteristic PP-fold (Saudek, V. et al. Biochemistry 1990, 29, 4509-4515). Furthermore, NPY sequences from a number of animal species have been elucidated and all show a high degree of amino acid homology to the human protein (more than 94% in rat, dog, rabbit, pig, cow, sheep) (see Larhammar, D. in "The Biology of Neuropeptide Y and Related Peptides", Colmers, W. F. and Wahlestedt, C. Eds., Humana Press, Totowa, N.J. 1993).

Endogenous receptor proteins that bind NPY and related peptides as ligands have been identified and distinguished, and several such proteins have been cloned and expressed. Six different receptor subtypes [$Y_1$, $Y_2$, $Y_3$, $Y_4$(PP), $Y_5$, $Y_6$ (formerly designated as a $Y_5$ receptor)] are recognized based upon binding profile, pharmacology, and/or composition if identity is known (Wahlestedt, C. et al. Ann. N.Y. Acad. Sci. 1990, 611, 7; Larhammar, D. et al. J. Biol. Chem. 1992, 267, 10935; Wahlestedt, C. et al. Regul. Pept. 1986, 13, 307; Fuhlendorff, J. U. et al. Proc. Natl. Acad. Sci. U.S.A. 1990, 87, 182; Grundemar, L. et al. J. Pharmacol. Exp. Ther. 1991, 258, 633; Laburthe, M. et al. Endocrinology 1986, 118, 1910; Castan, I. et al. Endocrinology 1992, 131, 1970; Gerald, C. et al. Nature 1996, 382, 168; Weinberg, D. H. et al. J. Biol. Chem. 1996, 271, 16435; Gehlert, D. et al. Curr. Pharm. Des. 1995, 1, 295; Lundberg, J. M. et al. Trends Pharmacol. Sci. 1996, 17, 301). Most and perhaps all NPY receptor proteins belong to the family of so-called G-protein coupled receptors (GPCRs).

NPY itself is the archetypal substrate for the NPY receptors and its binding can elicit a variety of pharmacological and biological effects in vitro and in vivo. When administered to the brain of live animals (Antracerebroventricularly (Acv) or into the amygdala), NPY produced anxiolytic effects in established animal models of anxiety such as the elevated plus-maze, Vogel punished drinking, and Geller-Seifter's bar-pressing conflict paradigms (Heilig, M. et al. Psychopharmacology 1989, 98, 524; Heilig, M. et al. Regul. Pept. 1992, 41, 61; Heilig, M. et al. Neuropsychopharmacology 1993, 8, 357). Thus, compounds that mimic NPY are postulated to be useful for the treatment of anxiolytic disorders.

The immunoreactivity of NPY is notably decreased in the cerebrospinal fluid of patients with major depression and those of suicide victims (Widdowson, P. S. et al. J. Neurochem. 1992, 59, 73), and rats treated with tricyclic antidepressants displayed significant increases of NPY relative to a control group (Heilig, M. et al. Eur. J. Pharmacol. 1988, 147, 465). These findings suggest that an inadequate NPY response may play a role in some depressive illnesses, and that compounds that regulate the NPY-ergic system may be useful for the treatment of depression.

It is known that the anxiolytic properties of NPY are mediated through postsynaptic $Y_1$ receptors, whereas presynaptic $Y_2$ receptors negatively control the release of NPY and other cotransmitters (e.g. GABA). Consequently, antagonism of the $Y_2$ receptor may lead to enhanced GABAergic and NPY-ergic effects and $Y_2$ receptor antagonists should prove useful in the treatment of depression and anxiety.

NPY improved memory and performance scores in animal models of learning (Flood, J. F. et al. Brain Res. 1987, 421, 280) and therefore may serve as a cognition enhancer for the treatment of neurodegenerative diseases such as Alzheimer's Disease (AD) as well as AIDS-related and senile dementia.

Elevated plasma levels of NPY were present in animals and humans experiencing episodes of high sympathetic nerve activity such as surgery, newborn delivery, and hemorrhage (Morris, M. J. et. al. J. Auton. Nerv. Syst. 1986, 17, 143). Thus, chemical substances that alter the NPY-ergic system may be useful for alleviating migraine, pain, and the condition of stress.

NPY also mediates endocrine functions such as the release of luteinizing hormone (LH) in rodents (Kalra, S. P. et. al. Front. Neuroendrocrinol. 1992, 13, 1). Since LH is vital for mammalian ovulation, a compound that mimics the action of NPY could be useful for the treatment of infertility, particularly in women with so-called luteal phase defects.

NPY is a powerful stimulant of food intake; as little as one-billionth of a gram, when injected directly into the CNS, caused satiated rats to overeat (Clark, J. T. et al. Endocrinology 1984, 115, 427; Levine, A. S. et al. Peptides 1984, 5, 1025; Stanley, B. G. et al. Life Sci. 1984, 35, 2635; Stanley, B. G. et al. Proc. Nat. Acad. Sci. U.S.A. 1985, 82, 3940). Thus NPY is orexigenic in rodents but not anxiogenic when given intracerebroventricularly and so antagonism of neuropeptide receptors may be useful for the treatment of diabetes and eating disorders such as obesity, anorexia nervosa, and bulimia nervosa.

Recently, a key role of presynaptic hypothalamic Y2 receptor was suggested in central coordination of energy homeostasis and bone mass regulation (Herzog, H. et al. Drug News & Perspectives 2002, 15, 506-510). Studies analyzing $Y_2$ receptor knockout mice have started to unravel some of the individual functions of this receptor subtype. $Y_2$ receptor knockout mice showed a reduced body weight despite an increase in food intake, possibly due to the lack of the feedback inhibition of the postprandially released $PYY_{3-36}$ (Batterham, R. L. et al. Nature 2002, 418, 650-654). The $Y_2$ receptor knockout mice also showed a significant increase in bone formation (Baldock, P. A. J. Clin. Invest. 2002, 109, 915-921). Specific deletion of the $Y_2$ receptor in the hypothalamus in adult conditional $Y_2$ receptor knockout mice also caused an increase in bone formation.

Studies have also indicates that NPY $Y_2$ is involved in the neurobiological responses to ethanol and other drugs of abuse. Thiele and coworkers (Neuropeptides, 2004, 38(4), 235-243; Peptides 2004, 25(6), 975-983) described the low ethanol consumption of $Y_2$ receptor knockout mice, as well as their increased voluntary water consumption. Therefore, modulators of NPY $Y_2$ may allow for the treatment of alcohol and drug abuse.

Grouzmann and coworkers described a peptide-based ligand, T4-[NPY 33-36], which showed considerable affinity ($AC_{50}$=67 nM) for the NPY $Y_2$ receptor (Grouzmann, E., et al. J. Biol. Chem. 1997, 272, 7699-7706). BIIE0246 also bound to the NYP $Y_2$ receptor with significant affinity ($AC_{50}$=3.3 nM) (Doods, H., et al. Eur. J. Pharmacol. 1999, 384, R3-R5). However, the therapeutic potential for these compounds is limited due to their peptide-like composition and elevated molecular weight.

There remains however, a need for potent NPY $Y_2$ modulators with desirable pharmaceutical properties.

Meerpoel, L., et al., in PCT Publication WO2202/020501, published Mar. 14, 2002, disclose polyarylcarboxamides useful as lipid lowering agents.

SUMMARY OF THE INVENTION

The present invention is directed to a compound of formula (A)

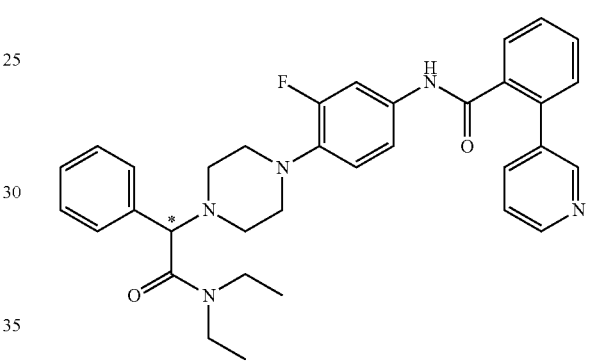

also known as N-{4-[4-(diethylcarbamoyl-phenyl-methyl)-piperazin-1-yl]-3-fluoro-phenyl}-2-pyridin-3-yl-benzamide; enantiomers thereof and pharmaceutically acceptable salts thereof.

The present invention is further directed to a compound of formula (B)

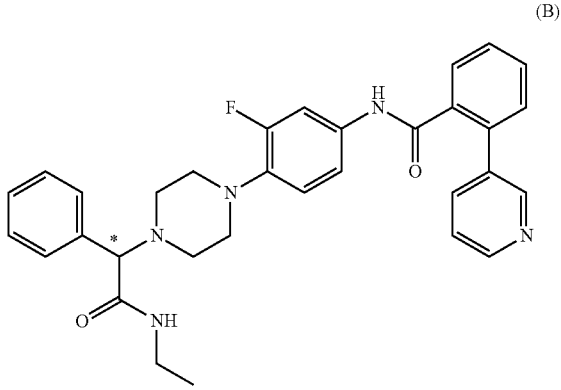

also known as N-{4-[4-(ethylcarbamoyl-phenyl-methyl)-piperazin-1-yl]-3-fluorophenyl}-2-pyridin-3-yl-benzamide; enantiomers thereof and pharmaceutically acceptable salts thereof.

In additional embodiments, the present invention is directed to the (R) and (S) enantiomers of the compounds of formula (A), and to the (R) and (S) enantiomers of the compound of formula (B). In additional embodiments, the present invention is directed to the (+) and (−) enantiomers of the compound of formula (A), and to the (+) and (−) enantiomers of the compound of formula (B).

Illustrative of the invention is a pharmaceutical composition comprising a pharmaceutically acceptable carrier and any of the compounds described herein. An illustration of the invention is a pharmaceutical composition made by mixing any of the compounds described herein and a pharmaceutically acceptable carrier. Illustrating the invention is a process for making a pharmaceutical composition comprising mixing any of the compounds described herein and a pharmaceutically acceptable carrier.

Exemplifying the invention are methods of treating a disorder mediated by the neuropeptide $Y_2$ receptor (selected from the group consisting of anxiolytic disorders, depression; pain, injured mammalian nerve tissue; conditions responsive to treatment with a neurotrophic factor; neurological disorders; bone loss; cardiovascular diseases; sleep-wake state disorders, substance abuse and addiction related disorders; obesity; obesity-related disorders, disorders responsive to modulation of endocrine function, inovulation and infertility; comprising administering to a subject in need thereof a therapeutically effective amount of any of the compounds or pharmaceutical compositions described above.

Another example of the invention is the use of any of the compounds described herein in the preparation of a medicament for treating: (a) anxiolytic disorders, (b) depression; (c) pain, (d) injured mammalian nerve tissue; (d) conditions responsive to treatment with a neurotrophic factor; (e) neurological disorders; (f) bone loss; (g) cardiovascular diseases; (h) sleep-wake state disorders, (i) substance abuse and addiction related disorders; (j) obesity; (k) obesity-related disorders, (l) disorders responsive to modulation of endocrine function (more particularly, disorders responsive to modulation of the pituitary and/or hypothalamic gland); (m) inovulation; and (n) infertility; in a subject in need thereof.

DETAILED DESCRIPTION OF THE INVENTION

Figure 1:
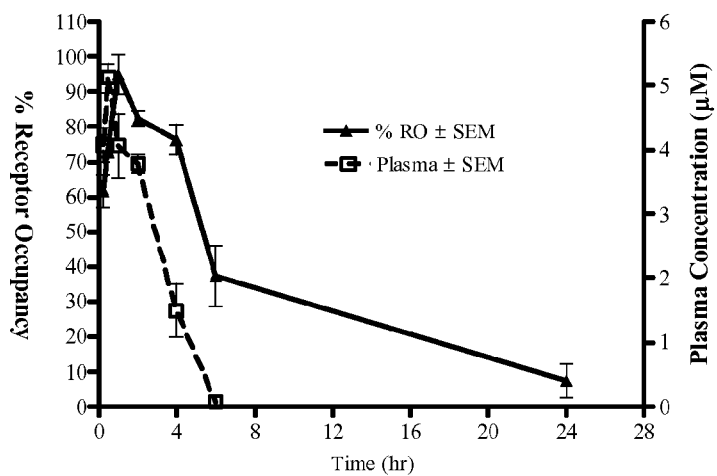
FIG. 1 illustrates ex vivo $Y_2$ receptor occupancy in rat hippocampus for the compound of formula (A) after SC administration at 10 mg/kg and corresponding rat plasma concentrations for the compound of formula (A).

The present invention is directed a compound of formula (A),

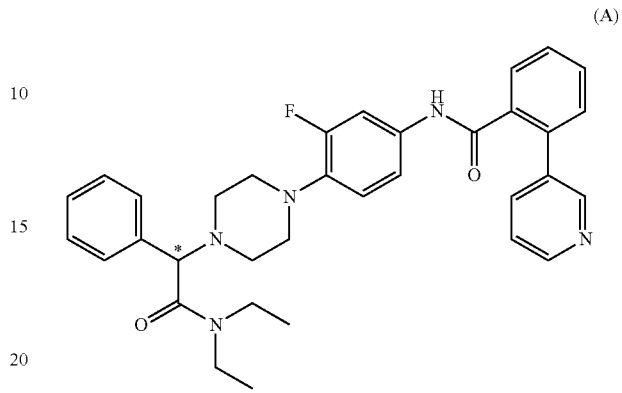

(A)

enantiomers thereof and pharmaceutically acceptable salts thereof; and further directed to a compound of formula (B)

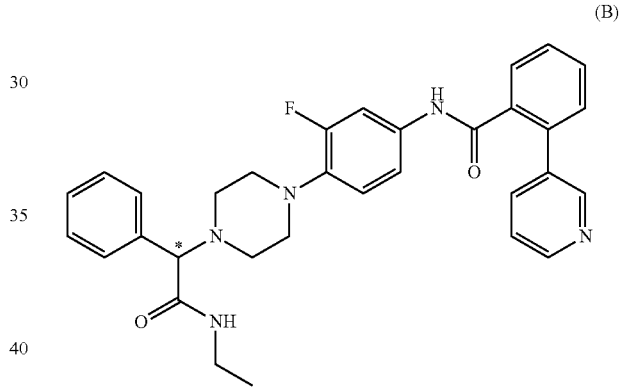

(B)

enantiomers thereof and pharmaceutically acceptable salts thereof. The compounds of the present invention are modulators of the NPY $Y_2$ receptor, useful in the treatment of disorders and conditions including, but not limited to anxiolytic disorders, depression; pain, injured mammalian nerve tissue; conditions responsive to treatment with a neurotrophic factor; neurological disorders; bone loss; cardiovascular diseases; sleep-wake state disorders, substance abuse and addiction related disorders; obesity; obesity-related disorders, disorders responsive to modulation of endocrine function, inovulation and infertility.

As used herein, unless otherwise noted, the term "anxiolytic disorders" shall be defined to include anxiety and related disorders including generalized anxiety disorder, acute stress disorder, post traumatic stress disorder, obsessive-compulsive disorder, social phobia (also known as social anxiety disorder), specific phobia, panic disorder with or without agoraphobia, agoraphobia without a history of panic disorder, anxiety disorder due to general medical condition, substance abuse induced anxiety disorder and anxiety disorder not otherwise specified (as these conditions are described by their diagnostic criteria, as listed in the *Diagnostic and*

*Statistical Manual of Mental Disorders*, 4th Edition, Text Revision, American Psychiatric Association, 2000, incorporated herein by reference). Anxiolytic disorders shall further include stress disorders including but not limited to hemorrhagic stress, stress-induced psychotic episodes, psychosocial dwarfism, stress headaches, stress-induced immune systems disorders such as stress-induced fever, and stress-related sleep disorders. Preferably, the anxiety or related disorder is selected from the group consisting of generalized anxiety disorder, acute stress disorder, post traumatic stress disorder and obsessive-compulsive disorder. More preferably, the anxiety and related disorder is generalized anxiety disorder.

As used herein, unless otherwise noted, the term "depression" shall be defined to include major depressive disorder (including single episode and recurrent), unipolar depression, treatment-refractory depression, resistant depression, anxious depression, dysthymia (also referred to as dysthymic disorder) as well as bipolar or manic disorders. Further, the term "depression" shall encompass any major depressive disorder, dysthymic disorder and depressive disorder not otherwise specific as defined by their diagnostic criteria, as listed in the *Diagnostic and Statistical Manual of Mental Disorders*, 4th Edition, Text Revision, American Psychiatric Association, 2000. Preferably, the depression is major depressive disorder, unipolar depression, treatment-refractory depression, resistant depression or anxious depression. More preferably, the depression is major depressive disorder.

As used herein, unless otherwise noted, the term "neurological disorders" include CNS disorders such as tinitus, spasticity, and neuropathic pain, supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, and disorders of pain perception such as fibromyalgia and epilepsy.

As used herein, the term "pain" shall be defined to include acute, chronic, inflammatory and neuropathic pain (preferably diabetic neuropathy). Further, the pain may be centrally mediated, peripherally mediated, caused by structural tissue injury, caused by soft tissue injury or caused by progressive disease. Any centrally mediated, peripherally mediated, structural tissue injury, soft tissue injury or progressive disease related pain may be acute or chronic.

As used herein, unless otherwise noted, pain shall include inflammatory pain, centrally mediated pain, peripherally mediated pain, visceral pain, structural related pain, cancer pain, soft tissue injury related pain, progressive disease related pain, neuropathic pain, acute pain from acute injury, acute pain from trauma, acute pain from surgery, headache, dental pain, back pain (preferably lower back pain), chronic pain from neuropathic conditions and chronic pain from post-stroke conditions.

"Nerve tissue" as used herein refers to any vertebrate nerve tissue, particularly including mammalian cells of the central nervous system (CNS) and peripheral nervous system (PNS). More particularly, nerve tissue includes spinal cord neuronal structures, peripheral nervous system nerves, and even nerve cells of the brain. "Nerve tissue injury", "injured mammalian nerve tissue", or "CNS or PNS nerve tissue injury" include any damage to relevant nerve tissue irrespective of cause, e.g., injuries attributable to trauma including but not limited to nerve tissue lesions, traumatically-induced compression, tumors, hemorrhage, infectious processes, spinal stenosis, or impaired blood supply.

"Treating injured mammalian nerve tissue" includes, but is not limited to, the in vivo administration of compounds, compositions, and methods of the instant invention to restore action potential or nerve impulse conduction through a nerve tissue lesion. The term may also include such administration in an effort to reduce the damaging effects of any injury to mammalian nerve tissue, whether through restoration of action potential or nerve impulse conduction, by stimulating growth or proliferation of nervous tissue, by ameliorating unwanted conditions in the extracellular microenvironment near an injury, or otherwise.

As used herein, unless otherwise noted, the term "cardiovascular diseases" shall include, for example, cardiac arrhythmia, post-myocardial infarction, and heart failure.

As used herein, unless otherwise noted, the term "sleep-wake state disorders" shall include narcolepsy; sleep apnea disorders such as central sleep apnea, obstructive sleep apnea, and mixed sleep apnea; hypersomnia, including excessive daytime sleepiness (EDS), and, in particular, hypersomnia associated with narcolepsy or sleep apnea disorder; sleep/wake disturbances associated with attention deficit hyperactive disorder (ADHD); circadian rhythm abnormalities such as delayed sleep phase syndrome, advance sleep phase syndrome, non-24 hour sleep/wake disorder, jet lag, or shift-work disorder; parasomnia disorders such as somnambulism, pavor nocturnus, REM sleep behavior disorder, sleep bruxism, or sleep enuresis; sleep-related movement disorders such as sleep bruxism, restless legs syndrome, or periodic limb movement; insomnia, including extrinsic insomnia, psychophysiologic insomnia, drug-dependent insomnia, or alcohol-dependent insomnia; sleep/wake disturbances associated with mental disorders such as depression, anxiety, schizophrenia, or other psychotic disorders; sleep/wake disturbances associated with neurological disorders such as migraine, epilepsy, Parkinson's disease, or Alzheimer's disease; and sleep/wake disturbances associated with fibromyalgia, headaches, gastroesophageal reflux disease, coronary artery ischemia, cardiac arrhythmias, abnormal swallowing, choking, or laryngospasm.

As used herein, unless otherwise noted the term "substance" when referring to substances of abuse and/or addiction shall include any legal or illegal substance to which a subject or patient may develop an addiction. Suitable examples include, but are not limited to alcohol, amphetamines (such as, for example, 3,4-methylene-dioxy-N-methylamphetamine, also known as "MDMA" or "ecstacy"), cannabis, hallucinogens (such as, for example, cocaine), inhalants, heroine, ketamine, Ecstacy, nicotine, oxycontin/oxycodone, codeine, morphine, opiods, phencyclidine, narcotics, or sedatives, or combinations thereof.

As used herein, unless otherwise noted, the term "substance abuse and addiction related disorders" shall include misuse, addiction, and/or dependence disorders related to substances of abuse. "Substance abuse and addiction related disorders" shall further include cravings, symptoms of withdrawal, and the like, associated with the misuse, addiction and/or dependency to substances of abuse.

As used herein, the term "obesity" shall be defined as a body mass index (BMI) of greater than or equal to about 25, preferably a BMI of greater than or equal to about 30. (The body mass index and other definitions are according to the "NIH Clinical Guidelines on the Identification and Evaluation, and Treatment of Overweight and Obesity in Adults" (1998)) Thus as used herein, the term "obesity" shall include both overweight and clinically obese subjects/patients.

As used herein, unless otherwise noted, the term "obesity-related disorders" shall include anorexia nervosa, wasting, AIDS-related weight loss, bulimia, cachexia, lipid disorders including hyperlipidemia and hyperuricemia, insulin resistance, noninsulin dependent diabetes mellitus (NIDDM, or Type II diabetes), insulin dependent diabetes mellitus (IDDM or Type I diabetes), diabetes-related complications including microangiopathic lesions, ocular lesions, retinopathy, neuropathy, and renal lesions, cardiovascular disease including cardiac insufficiency, coronary insufficiency, and high blood pressure, atherosclerosis, atheromatous disease, stroke, hypertension, Syndrome X, gallbladder disease, osteoarthritis, sleep apnea, forms of cancer such as uterine, breast, colorectal, kidney, and gallbladder, high cholesterol levels, complications of pregnancy, menstrual irregularities, hirsutism, muscular dystrophy, infertility, and increased surgical risk.

As used herein, unless otherwise noted, the term "disorders responsive to modulation of endocrine function (more particularly, disorders responsive to modulation of the pituitary and/or hypothalamic gland)" include, but are not limited to elevated glucose level, pre-diabetes, impaired oral glucose tolerance, poor glycemic control, Type II Diabetes Mellitus, Syndrome X (also known as metabolic syndrome), gestational diabetes, insulin resistance, hyperglycemia and loss of muscle mass as a results of hyperglycemia (cachexia), ifertility, inovulation, and the like. Further, the term "metabolic disorders" shall include disorders related to the metabolic system, including, but not limited to elevated glucose level, pre-diabetes, impaired oral glucose tolerance, poor glycemic control, Type II Diabetes Mellitus, Syndrome X (also known as metabolic syndrome), gestational diabetes, insulin resistance, hyperglycemia, and the like.

"Neurotrophic factor", as used herein, refers to compounds that are capable of stimulating growth or proliferation of nervous tissue, including compounds of the instant invention and known neurotrophic factors described previously herein. Thus, the term "disorders responsive to treatment through administration of a neurotrophic factor" shall refer to any disorder which whose symptoms, pathways and/or progression may be treated and/or prevented through the use of a neurotropic factor agent.

As used herein, unless otherwise noted, the term "bone loss" refers to enhancement of bone growth or prevention of bone loss caused by conditions such as osteoporosis, osteomalacia, Paget's disease, disorders of bone homeostasis, and the like.

As used herein, unless otherwise noted, the term "infertility" shall include both male and female infertility. As used herein, unless otherwise noted, the term "inovulation" shall include inovulation regardless of underlying cause.

Abbreviations used in the specification, particularly the Schemes and Examples, are as follows:

AIBN=2-Azobisisobutyronitrile

DIPEA=N-Ethyldiisopropylamine

DMEM=Dulbecco's Modified Eagle's Medium

DMF=N,N-Dimethylformamide

DMSO=Dimethylsulfoxide

EDTA=Ethylene Diamine Tetraacetic Acid $Et_3N$=Triethylamine

EtOAc=Ethyl acetate

EtOH=Ethanol

HATU=O-(7-Azabenzotriazol-1-yl)-N,N,N",N"-Tetramethyl Uronium Hexafluorophosphate HEPES=4-(2-Hydroxyethyl)-1-Piperizine Ethane Sulfonic Acid Hex=Hexanes HPLC=High Pressure Liquid Chromatography MeOH=Methanol MTBE=Methyl t-butyl ether MTP=Microsomal Triglyceride Transfer Protein PTLC=Preparative Thin Layer Chromatography THF=Tetrahydrofuran TLC=Thin Layer Chromatography Tris HCl or Tris-Cl=Tris[hydroxymethyl]aminomethyl hydrochloride As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

One skilled in the art will note that, as listed in the Examples which follow herein, the optical rotation was measured for the enantiomers of the compound of formula (A) and the compound of formula (B). Exact stereo-orientation, as measured for example by single crystal X-ray diffraction, was not determined.

In an embodiment, the present invention is directed to the (S) enantiomer of the compound of formula (A), a compound of formula (A-S) as shown below (A-S)

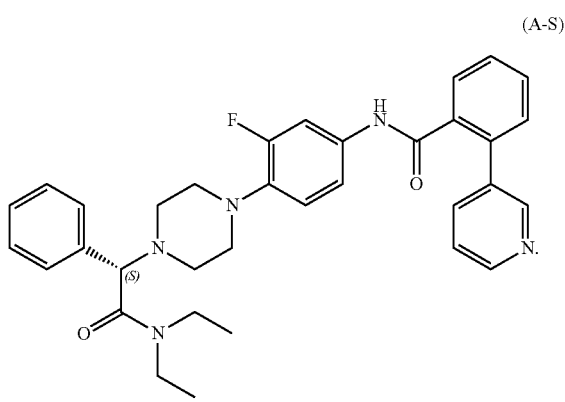

In another embodiment, the present invention is directed to the (R) enantiomer of the compound of formula (A), a compound of formula (A-R) as shown below (A-R)

In an embodiment, the present invention is directed to the (S) enantiomer of the compound of formula (B), a compound of formula (B-S) as shown below (B-S)

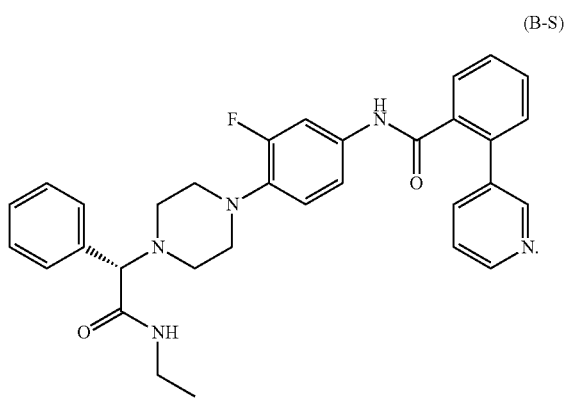

In another embodiment, the present invention is directed to the (R) enantiomer of the compound of formula (B), a compound of formula (B-R) as shown below (B-R)

In an embodiment of the present invention, the compound of formula (A-S) is present in an enantiomeric excess of greater than or equal to about 50%. In another embodiment of the present invention, the compound of formula (A-S) is present in an enantiomeric excess of greater than or equal to about 75%. In another embodiment of the present invention, the compound of formula (A-S) is present in an enantiomeric excess of greater than or equal to about 85%. In another embodiment of the present invention, the compound of formula (A-S) is present in an enantiomeric excess of greater than or equal to about 90%. In another embodiment of the present invention, the compound of formula (A-S) is present in an enantiomeric excess of greater than or equal to about 95%. In another embodiment of the present invention, the compound of formula (A-S) is present in an enantiomeric excess of greater than or equal to about 98%. In another embodiment of the present invention, the compound of formula (A-S) is present in an enantiomeric excess of greater than or equal to about 99%.

In an embodiment of the present invention, the compound of formula (A-R) is present in an enantiomeric excess of greater than or equal to about 50%. In another embodiment of the present invention, the compound of formula (A-R) is present in an enantiomeric excess of greater than or equal to about 75%. In another embodiment of the present invention, the compound of formula (A-R) is present in an enantiomeric excess of greater than or equal to about 85%. In another embodiment of the present invention, the compound of formula (A-R) is present in an enantiomeric excess of greater than or equal to about 90%. In another embodiment of the present invention, the compound of formula (A-R) is present in an enantiomeric excess of greater than or equal to about 95%. In another embodiment of the present invention, the compound of formula (A-R) is present in an enantiomeric excess of greater than or equal to about 98%. In another embodiment of the present invention, the compound of formula (A-R) is present in an enantiomeric excess of greater than or equal to about 99%.

In an embodiment of the present invention, the (+) enantiomer of the compound of formula (A) is present in an enantiomeric excess of greater than or equal to about 50%. In another embodiment of the present invention, the (+) enantiomer of the compound of formula (A) is present in an enantiomeric excess of greater than or equal to about 75%. In another embodiment of the present invention, the (+) enantiomer of the compound of formula (A) is present in an enantiomeric excess of greater than or equal to about 85%. In another embodiment of the present invention, the (+) enantiomer of the compound of formula (A) is present in an enantiomeric excess of greater than or equal to about 90%. In another embodiment of the present invention, the (+) enantiomer of the compound of formula (A) is present in an enantiomeric excess of greater than or equal to about 95%. In another embodiment of the present invention, the (+) enantiomer of the compound of formula (A) is present in an enantiomeric excess of greater than or equal to about 98%. In another embodiment of the present invention, the (+) enantiomer of the compound of formula (A) is present in an enantiomeric excess of greater than or equal to about 99%.

In an embodiment of the present invention, the (−) enantiomer of the compound of formula (A) is present in an enantiomeric excess of greater than or equal to about 50%. In another embodiment of the present invention, the (−) enantiomer of the compound of formula (A) is present in an enantiomeric excess of greater than or equal to about 75%. In another embodiment of the present invention, the (−) enantiomer of the compound of formula (A) is present in an enantiomeric excess of greater than or equal to about 85%. In another embodiment of the present invention, the (−) enantiomer of the compound of formula (A) is present in an enantiomeric excess of greater than or equal to about 90%. In another embodiment of the present invention, the (−) enantiomer of the compound of formula (A) is present in an enantiomeric excess of greater than or equal to about 95%. In another embodiment of the present invention, the (−) enantiomer of the compound of formula (A) is present in an enantiomeric excess of greater than or equal to about 98%. In another embodiment of the present invention, the (−) enantiomer of the compound of formula (A) is present in an enantiomeric excess of greater than or equal to about 99%.

In an embodiment of the present invention, the compound of formula (B-S) is present in an enantiomeric excess of greater than or equal to about 50%. In another embodiment of the present invention, the compound of formula (B-S) is present in an enantiomeric excess of greater than or equal to about 75%. In another embodiment of the present invention, the compound of formula (B-S) is present in an enantiomeric excess of greater than or equal to about 85%. In another embodiment of the present invention, the compound of formula (B-S) is present in an enantiomeric excess of greater than or equal to about 90%. In another embodiment of the present invention, the compound of formula (B-S) is present in an enantiomeric excess of greater than or equal to about 95%. In another embodiment of the present invention, the compound of formula (B-S) is present in an enantiomeric excess of greater than or equal to about 98%. In another embodiment of the present invention, the compound of formula (B-S) is present in an enantiomeric excess of greater than or equal to about 99%.

In an embodiment of the present invention, the compound of formula (B-R) is present in an enantiomeric excess of greater than or equal to about 50%. In another embodiment of the present invention, the compound of formula (B-R) is present in an enantiomeric excess of greater than or equal to about 75%. In another embodiment of the present invention, the compound of formula (B-R) is present in an enantiomeric excess of greater than or equal to about 85%. In another embodiment of the present invention, the compound of formula (B-R) is present in an enantiomeric excess of greater than or equal to about 90%. In another embodiment of the present invention, the compound of formula (B-R) is present in an enantiomeric excess of greater than or equal to about 95%. In another embodiment of the present invention, the compound of formula (B-R) is present in an enantiomeric excess of greater than or equal to about 98%. In another embodiment of the present invention, the compound of formula (B-R) is present in an enantiomeric excess of greater than or equal to about 99%.

In an embodiment of the present invention, the (+) enantiomer of the compound of formula (B) is present in an enantiomeric excess of greater than or equal to about 50%. In another embodiment of the present invention, the (+) enantiomer of the compound of formula (B) is present in an enantiomeric excess of greater than or equal to about 75%. In another embodiment of the present invention, the (+) enantiomer of the compound of formula (B) is present in an enantiomeric excess of greater than or equal to about 85%. In another embodiment of the present invention, the (+) enantiomer of the compound of formula (B) is present in an enantiomeric excess of greater than or equal to about 90%. In another embodiment of the present invention, the (+) enantiomer of the compound of formula (B) is present in an enantiomeric excess of greater than or equal to about 95%. In another embodiment of the present invention, the (+) enantiomer of the compound of formula (B) is present in an enantiomeric excess of greater than or equal to about 98%. In another embodiment of the present invention, the (+) enantiomer of the compound of formula (B) is present in an enantiomeric excess of greater than or equal to about 99%.

In an embodiment of the present invention, the (−) enantiomer of the compound of formula (B) is present in an enantiomeric excess of greater than or equal to about 50%. In another embodiment of the present invention, the (−) enantiomer of the compound of formula (B) is present in an enantiomeric excess of greater than or equal to about 75%. In another embodiment of the present invention, the (−) enantiomer of the compound of formula (B) is present in an enantiomeric excess of greater than or equal to about 85%. In another embodiment of the present invention, the (−) enantiomer of the compound of formula (B) is present in an enantiomeric excess of greater than or equal to about 90%. In another embodiment of the present invention, the (−) enantiomer of the compound of formula (B) is present in an enantiomeric excess of greater than or equal to about 95%. In another embodiment of the present invention, the (−) enantiomer of the compound of formula (B) is present in an enantiomeric excess of greater than or equal to about 98%. In another embodiment of the present invention, the (−) enantiomer of the compound of formula (B) is present in an enantiomeric excess of greater than or equal to about 99%.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, a-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In an embodiment, the present invention is directed to a pharmaceutically acceptable salt of compound of formula (A). In another embodiment of the present invention, the pharmaceutically acceptable salt of the compound of formula (A) is selected from the group consisting of citrate, maleate and HCl salts of the compound of formula (A), preferably, a HCl salt of the compound of formula (A), more preferably, a bis-HCl salt of the compound of formula (A).

The pharmaceutically acceptable salts of the compounds of the present invention may be prepared by reacting the selected compound with a suitably selected acid. For example, the HCl salt (preferably, the bis-HCl) of the compound of formula (A) may be prepared by reacting the compound of formula (A) with HCl in for example, absolute ethanol. Similarly, the maleate salt of the compound of formula (A) may be prepared by reacting the compound of formula (A) with maleic acid, in for example, absolute ethanol. Similarly, the citrate salt of the compound of formula (A) may be prepared by reacting the compound of formula (A) with citric acid, in for example, absolute ethanol.

The compounds and pharmaceutically acceptable salts described herein may be isolated as amorphous, partially crystalline or crystalline forms. Some of the crystalline forms may exist as polymorphs and as such are intended to be included in the present invention. In addition, the compounds and pharmaceutically acceptable salts of the present invention may form solvates with water (i.e., hydrates) or common organic solvents, and such solvates are also intended to be encompassed within the scope of this invention.

As used herein, unless otherwise noted, the term "isolated form" shall mean that the compound is present in a form which is separate from any solid mixture with another compound(s), solvent system or biological environment. In an embodiment, the present invention is directed to an isolated form of any of the compounds described herein.

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, any of the compounds described herein are substantially pure.

As used herein, unless otherwise noted, the term "substantially free of a corresponding salt form(s)" when used to described any of the compounds disclosed herein shall mean that the mole percent of any corresponding salt form(s) in the isolated compound is less than about 5 mole percent, preferably less than about 2 mole percent, more preferably, less than about 0.5 mole percent, most preferably less than about 0.1 mole percent. In an embodiment of the present invention, any of the compounds described herein is substantially free of corresponding salt forms.

In an embodiment of the present invention, the compound of formula (A), the compound of formula (A-R) or the compound of formula (A-S) is present as a substantially pure compound. In another embodiment of the present invention, the compound of formula (A), the compound of formula (A-R) or the compound of formula (A-S) is present in a form which is substantially free of a corresponding salt form(s). In another embodiment of the present invention, the compound of formula (A), the compound of formula (A-R) or the compound of formula (A-S) is present as its corresponding pharmaceutically acceptable salt. In another embodiment of the present invention, the compound of formula (A), the compound of formula (A-R) or the compound of formula (A-S) is present in an isolated form.

In an embodiment of the present invention, the compound of formula (B), the compound of formula (B-R) or the compound of formula (B-S) is present as a substantially pure compound. In another embodiment of the present invention, the compound of formula (B), the compound of formula (B-R) or the compound of formula (B-S) is present in a form which is substantially free of a corresponding salt form(s). In another embodiment of the present invention, the compound of formula (B), the compound of formula (B-R) or the compound of formula (B-S) is present as its corresponding pharmaceutically acceptable salt. In another embodiment of the present invention, the compound of formula (B), the compound of formula (B-R) or the compound of formula (B-S) is present in an isolated form.

In an embodiment of the present invention, the compound of formula (A), the (+) enantiomer of the compound of formula (A) or the (−) enantiomer of the compound of formula (A) is present as a substantially pure compound. In another embodiment of the present invention, the compound of formula (A), the (+) enantiomer of the compound of formula (A) or the (−) enantiomer of the compound of formula (A) is present in a form which is substantially free of a corresponding salt form(s). In another embodiment of the present invention, the compound of formula (A), the (+) enantiomer of the compound of formula (A) or the (−) enantiomer of the compound of formula (A) is present as its corresponding pharmaceutically acceptable salt. In another embodiment of the present invention, the compound of formula (A), the (+) enantiomer of the compound of formula (A) or the (−) enantiomer of the compound of formula (A) is present in an isolated form.

In an embodiment of the present invention, the compound of formula (B), the (+) enantiomer of the compound of formula (B) or the (−) enantiomer of the compound of formula (B) is present as a substantially pure compound. In another embodiment of the present invention, the compound of formula (B), the (+) enantiomer of the compound of formula (B) or the (−) enantiomer of the compound of formula (B) is present in a form which is substantially free of a corresponding salt form(s). In another embodiment of the present invention, the compound of formula (B), the (+) enantiomer of the compound of formula (B) or the (−) enantiomer of the compound of formula (B) is present as its corresponding pharmaceutically acceptable salt. In another embodiment of the present invention, the compound of formula (B), the (+) enantiomer of the compound of formula (B) or the (−) enantiomer of the compound of formula (B) is present in an isolated form.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One skilled in the art will recognize that, where not otherwise specified, the reaction step(s) is performed under suitable conditions, according to known methods, to provide the desired product.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention further comprises pharmaceutical compositions containing one or more of the compounds or pharmaceutically acceptable salts as described herein with a pharmaceutically acceptable carrier.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg or any range therein, and may be given at a dosage of from about 0.01-300 mg/kg/day, or any range therein, preferably from about 0.5-50 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any range therein; preferably about 10 to 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (A) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications,* Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by the NPY Y2 receptor is required.

The daily dosage of the products may be varied over a wide range from 0.01 to 1,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any range therein. Preferably, the range is from about 0.5 to about 50.0 mg/kg of body weight per day, or any range therein. More preferably, from about 1.0 to about 25.0 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

Bromo-phenyl-acetyl chloride

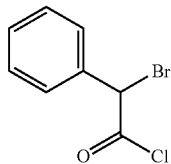

Phenyl acetyl chloride (29.6 g, 191.0 mmol) N-bromosuccinamide (34.1 g, 191 mmol) and AIBN (1.90 g, 11.7 mmol) were taken up in CCl$_4$ (220 mL) and the resulting mixture was heated at 80° C. for 6 h. The reaction mixture was then cooled to ambient temperature, following which hexanes were added to the reaction mixture. The solids that precipitated were removed by filtration and the filtrate was concentrated on a rotary evaporator to yield the title compound as a yellow oil. The yellow oil was used in the next step without further purification.

EXAMPLE 2

2-Bromo-N,N-diethyl-2-phenyl-acetamide

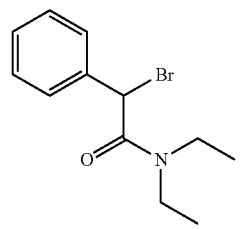

Bromo-phenyl-acetyl chloride (191.0 mmol) was taken up in anhydrous dichloromethane (150 mL) and the resulting mixture was cooled to 0° C. in an ice bath. Diethylamine (14.1 g, 191 mmol) was then added drop-wise over 15 minutes, following which DIPEA (24.7 g, 191 mmol) was added over 5 minutes. The reaction mixture was stirred at ambient temperature for 4 h. The reaction mixture was then washed with water, dried over MgSO$_4$, filtered and concentrated to yield a dark brown colored oil. The oil was purified by silica gel chromatography to yield the title compound as a yellow oil.

MS (ESI): mass calcd. for C$_{12}$H$_{16}$BrNO, 269.04; m/z found, 270.1 [M+H]$^+$.

$^1$H-NMR(400 MHz, CDCl$_3$) δ ppm: 7.14-7.07 (m, 5H), 3.26-3.23 (m, 4H), 1.22-1.18 (m, 6H).

EXAMPLE 3

N,N-Diethyl-2-[4-(2-fluoro-4-nitro-phenyl)-piperazin-1-yl]-2-phenyl-acetamide

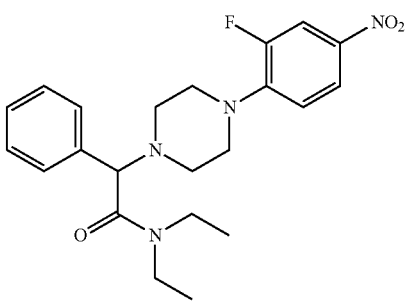

A 500 mL, round-bottomed flask under a positive pressure of nitrogen was equipped with a magnetic stirrer and charged with anhydrous DMF (100 mL), 1-(2-fluoro-4-nitro-phenyl)-piperazine (4.0 g, 17.8 mmol), anhydrous K$_2$CO$_3$ (4.9 g, 35.5 mmol) and 2-bromo-N,N-diethyl-2-phenyl-acetamide (6.2 g, 23.0 mmol). The pale yellow reaction mixture was stirred at ambient temperature for 4 h, following which the solvent was removed on the rotary evaporator to yield a yellow colored semi-solid. MTBE (250 mL) was added and the resulting suspension was stirred at ambient temperature for 0.5 h and then filtered. The filtrate was extracted with 1.5N HCl (1×200 mL, then 1×100 mL). The aqueous layers were pooled, cooled to ~0° C. in an ice bath and then basified with 2N NaOH (to pH ca. 13). The basified reaction mixture was extracted with MTBE (4×125 mL). The organic layers were pooled, dried over anhydrous sodium sulfate, filtered and concentrated to yield a brown colored oil. The oil was purified by silica gel chromatography (solvent: EtOAc/Hexane) to yield the title compound as a reddish-brown oil.

MS (ESI): mass calcd. for $C_{22}H_{27}FN_4O_3$, 414.21; m/z found, 415.1 $[M+H]^+$.

$^1$H-NMR(400 MHz, CDCl$_3$) δ ppm: 7.97-7.93 (m, 1H), 7.89-7.85 (m, 1H), 7.39-7.30 (m, 5H), 6.86 (t, J=8.8 Hz, 1H), 4.27(s, 1H), 3.51-3.44 (m, 1H), 3.41-3.24 (m, 6H), 3.21-3.13 (m, 1H), 2.79-2.65 (m, 4H), 1.09 (t, J=7.1 Hz, 3H), 1.03 (t, J=7.1 Hz, 3H).

EXAMPLE 4

2-[4-(4-Amino-2-fluoro-phenyl)-piperazin-1-yl]-N,N-diethyl-2-phenyl-acetamide

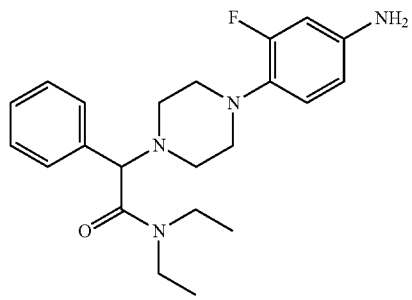

A 500 mL, round-bottomed flask under a positive pressure of nitrogen was equipped with a magnetic stirrer and charged with absolute ethanol (150 mL) followed by N,N-diethyl-2-[4-(2-fluoro-4-nitro-phenyl)piperazin-1-yl]-2-phenyl-acetamide (5.6 g, 13.5 mmol). To this stirred solution was added in one portion, SnCl$_2$.2H$_2$O (9.1 g, 40.3 mmol) and the reaction mixture was placed in a pre-heated oil bath maintained at ~85° C. for 8 h. The reaction mixture was cooled to ambient temperature and then concentrated on the rotary evaporator to yield a viscous orange-brown oil. To this oil was added saturated aqueous sodium carbonate solution (100 mL) and EtOAc (150 mL). The resulting biphasic suspension was stirred at ambient temperature for 0.5 h, then filtered through a pad of Celite®. The Celite® pad was washed with EtOAc (2×50 mL). The filtrates were combined and phases were separated. The aqueous layer was extracted with EtOAc (1×50 mL). The organic layers were pooled, and dried over anhydrous sodium sulfate, filtered and concentrated to yield the title compound as a reddish-brown oil, which was used in the next step without further purification.

MS (ESI): mass calcd. for $C_{22}H_{29}FN_4O$, 384.23; m/z found, 385.1 $[M+H]^+$.

EXAMPLE 5

N-{4-[4-(Diethylcarbamoyl-phenyl-methyl)-piperazin-1-yl]-3-fluoro-phenyl}-2-pyridin-3-yl-benzamide (Compound (A))

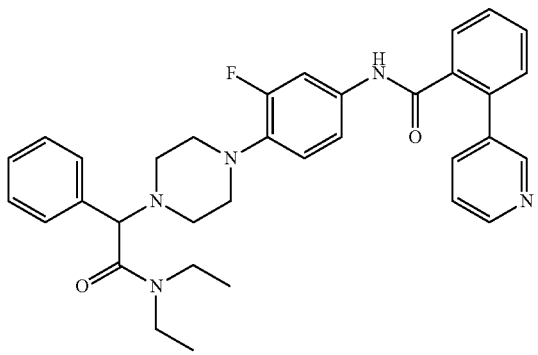

A 250 mL, round-bottomed flask under a positive pressure of nitrogen was equipped with a magnetic stirrer and charged with anhydrous DMF (70 mL) followed by 2-[4-(4-amino-2-fluoro-phenyl)-piperazin-1-yl]-N,N-diethyl-2-phenyl-acetamide (3.5 g, 9.1 mmol), 2-pyridin-3-yl-benzoic acid (1.9 g, 9.5 mmol), HATU (3.8 g, 10.0 mmol) and DIPEA (1.3 g, 10.0 mmol). The resulting brown colored reaction mixture was stirred at ambient temperature for 16 h. The reaction mixture was then concentrated on the rotary evaporator to yield an oil. To this oil was added, dichloromethane (100 mL) and 1N NaOH (50 mL). The biphasic solution was stirred for 0.5 h after which phases were separated. The aqueous layer was extracted with dichloromethane (2×25 mL). The organic layers were pooled, dried over anhydrous sodium sulfate, filtered and concentrated to yield a viscous brown oil. The oil was taken in ethanol (100 mL) and heated to ~60° C. in a water bath for 1 h. The resulting mixture was diluted with MTBE (added with magnetic stirring in 25 mL portions, total 125 mL). The resulting suspension was stirred at 0° C. (ice/water bath) for 2 h. The product was collected by filtration through a medium porosity glass frit, washed with a mixture of EtOH/MTBE (1:1.25, 22.5 mL×2) and the filter-cake dried thoroughly under house vacuum to yield the title compound as an off-white solid.

MS (ESI): mass calcd. for $C_{34}H_{36}FN_5O_2$, 565.29; m/z found, 566.4 $[M+H]^+$.

$^1$H-NMR(400 MHz, DMSO-d$_6$) δ ppm: 10.65 (s, 1H), 10.5 (bs, 1H), 8.92 (s, 1H), 8.82 (d, J=5.5 Hz, 1H), 8.39 (d, J=7.6 Hz, 1H), 7.96 (dd, J=7.8, 5.6 Hz, 1H), 7.76 (d, J=7.6 Hz, 1H), 7.70-7.63 (m, 4H), 7.56-7.50 (m, 4H), 7.26 (dd, J=8.7, 1.7 Hz, 1H), 7.02 (t, J=9.4 Hz, 1H), 5.97 (s, 1H), 3.63-3.61 (m, 1H), 3.48-3.15 (m, 10H), 2.67-2.65 (m, 1H), 1.10-1.01 (m, 3H), 0.82-0.80 (m, 3H).

EXAMPLE 6

N-{4-[4-(Diethylcarbamoyl-phenyl-methyl)-piperazin-1-yl]-3-fluoro-phenyl}-2-pyridin-3-yl-benzamide bis-hydrochloride

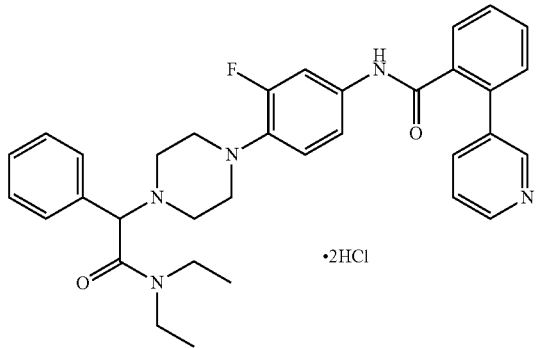

A 500 mL, round-bottomed flask under a positive pressure of nitrogen was equipped with a magnetic stirrer and charged with absolute ethanol (90 mL) followed by N-{4-[4-(diethylcarbamoyl-phenyl-methyl)-piperazin-1-yl]-3-fluoro-phenyl}-2-pyridin-3-yl-benzamide (4.5 g, 7.9 mmol). 2M HCl in anhydrous ether (7.9 mL, 15.9 mmol) was added drop-wise to the reaction mixture via an addition funnel and the resulting suspension was stirred at ambient temperature for 2 h. The reaction mixture was diluted by the addition of anhydrous ether (90 mL) in a slow stream, which resulted in a gummy solid. The solvents were removed on the rotary evaporator to yield a pale brown foam. The foam was triturated with a mixture of dichloromethane/ether (45 mL each) and the resulting suspension was stirred at ambient temperature for 3 h, then at 0° C. for 1 h. The resulting solid was collected by filtration and the filter-cake was washed with 1:1 dichloromethane/ether (2×40 mL) and dried under house vacuum. The powder was dried further on the rotary evaporator (water bath temperature 50° C.) to yield the title compound as an off-while solid.

MS (ESI): mass calcd. for $C_{34}H_{38}Cl_2FN_5O_2$, 637.24; m/z found, 566.2 [M+H]$^+$(free Base).

$^1$H-NMR(400 MHz, DMSO-$d_6$) δ ppm: 10.56 (s, 1H), 10.41 (bs, 1H), 8.84 (s, 1H), 8.78-8.73 (m, 1H), 8.28 (d, J=8.0 Hz, 1H), 7.88-7.82 (m, 1H), 7.75-7.45 (m, 10H), 7.30-7.20 (m, 1H), 7.01 (t, J=9.3 Hz, 1H), 5.89 (s, 1H), 3.63 (bs, 1H), 3.39-3.19 (m, 8H), 2.68 (bs, 1H), 1.03 (t, J=7.0 Hz, 3H), 0.82 (t, J=7.0 Hz, 3H).

EXAMPLE 7 & 8

(+) and (−)-N-{4-[4-(Diethylcarbamoyl-phenyl-methyl)-piperazin-1-yl]-3-fluoro-phenyl}-2-pyridin-3-yl-benzamide

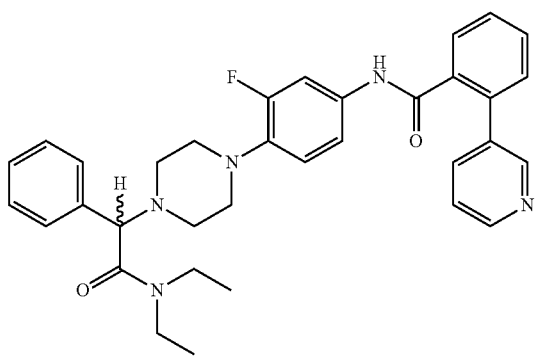

Racemic N-{4-[4-(Diethylcarbamoyl-phenyl-methyl)-piperazin-1-yl]-3-fluoro-phenyl}-2-pyridin-3-yl-benzamide (100 mg, 0.18 mmol) was separated by chiral HPLC using a Diacel IA column (Chiral Technologies) with a mobile phase of 10% 2-propanol:90% hexanes with a flow rate of 1.5 mL/min.

Fraction 1, (−)-Enantiomer (Retention Time 25.9 Minutes):
Optical Rotation [α]$^{20}_D$−26.6 (c=1.2, MeOH) found using a Perkin Elmer Model 341 Polarimter)

MS (ESI): mass calcd. for $C_{34}H_{36}FN_5O_2$, 565.29; m/z found, 566.4 [M+H]$^+$.

$^1$H-NMR(400 MHz, CDCl$_3$) δ ppm: 8.64 (s, 1H), 8.52 (d, J=4.8 Hz, 1H), 7.93 (s, 1H), 7.77 (s, 1H), 7.71 (d, J=7.6 Hz, 1H), 7.55-7.47 (m, 4H), 7.40-7.30 (m, 6H), 6.85-6.84 (m, 1H), 6.78-6.75 (m, 1H), 3.42-3.12 (m, 9H), 2.88-2.84 (m, 4H), 1.08-1.06 (t, 7.1 Hz, 3H), 1.02-0.98 (t, J=7.0 Hz, 3H).

Fraction 2 (+)-Enantiomer (Retention Time 31.4 Minutes):
Optical Rotation [α]$^{20}_D$+26.2 (c=1.2, MeOH) found using a Perkin Elmer Model 341 Polarimter)

MS (ESI): mass calcd. for $C_{34}H_{36}FN_5O_2$, 565.29; m/z found, 566.4 [M+H]$^+$.

$^1$H NMR (CDCl$_3$): 8.61 (s, 1H), 8.52 (d, J=4.0, 1H), 7.77 (d, J=7.8, 1H), 7.72 (d, J=7.6, 1H), 7.56-7.24 (m, 10H), 6.83-6.77 (m, 2H), 4.23 (s, 1H), 3.43-3.38 (m, 2H), 3.26-3.17 (m, 2H), 3.05 (s, 4H), 2.67 (bs, 4H), 1.07-1.02 (m, 6H).

EXAMPLE 9

4-(2-Fluoro-4-nitro-phenyl)-piperazine-1-carboxylic acid tert-butyl ester

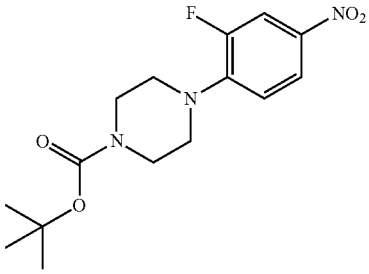

To a solution of 1-(2-fluoro-4-nitro-phenyl)-piperazine (6.33 g, 28.1 mmol) and DIPEA (3.83 g, 29.6 mmol) in CH$_2$Cl$_2$ (50.0 mL) was added a solution of di-tert-butyl dicarbonate (6.44 g, 29.6 mmol) in CH$_2$Cl$_2$ (50 mL). After 16 h, the reaction mixture was diluted with CH$_2$Cl$_2$ (100 mL) and washed with water. The organic layer was dried (MgSO$_4$) and concentrated to yield the title compound as a yellow solid.

MS: mass calcd. for $C_{15}H_{20}FN_3O_4$, 325.14; m/z found, 326.2 [M+H]$^+$.

EXAMPLE 10

4-(4-Amino-2-fluoro-phenyl)-piperazine-1-carboxylic acid tert-butyl ester

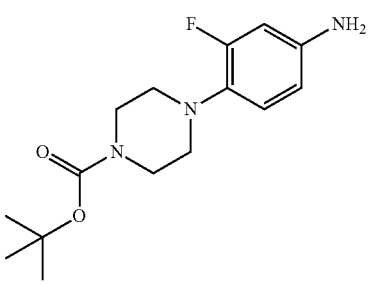

A solution of 4-(2-fluoro-4-nitro-phenyl)-piperazine-1-carboxylic acid tert-butyl ester (9.30 g, 28.6 mmol) in EtOH (80 mL) was treated with hydrogen (H$_2$, 50 psi) in the presence of 10% Pd/C (0.50 g). After 2.5 h, the reaction mixture was filtered and the filtrate was concentrated to yield the title compound.

MS: mass calcd. for C$_{15}$H$_{22}$FN$_3$O$_2$, 295.17; m/z found, 296.2 [M+H]$^+$.

$^1$H NMR (CDCl$_3$): 6.80-6.78 (m, 1H), 6.44-6.36 (m, 2H), 3.66-3.50 (m, 6H), 2.93-2.85 (m, 4H), 1.47 (s, 9H).

EXAMPLE 11

N-(3-Fluoro-4-piperazin-1-yl-phenyl)-2-pyridin-3-yl-benzamide

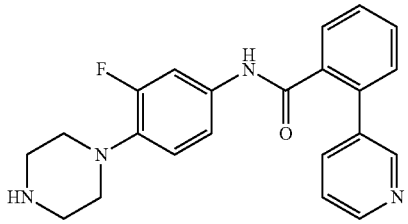

To a solution of 4-(4-Amino-2-fluoro-phenyl)-piperazine-1-carboxylic acid tert-butyl ester (1.00 g, 3.4 mmol) and 2-pyrid-3-yl benzoic acid (0.70 g, 3.7 mmol) in DMF (10 mL) was added HATU (1.42 g, 3.7 mmol) and diisopropylamine (0.65 mL, 3.7 mmol). After stirring at room temperature for 18 h, the reaction mixture was diluted with EtOAc (100 mL) and washed with H$_2$O (4×50 mL). The organic extracts were combined, dried (Na$_2$SO$_4$), and the solvent was evaporated under reduced pressure. Chromatography of the resulting residue (SiO$_2$: EtOAc:Hex) yielded 4-[2-fluoro-4-(2-pyridin-3-yl-benzoylamino)-phenyl]-piperazine-1-carboxylic acid tert-butyl ester which was further dissolved in MeOH (20 mL) and 4N HCl in dioxanes. After stirring for 5 h, the reaction mixture was concentrated down, neutralized with 1N NaOH, and extracted with EtOAc (3×75mL). The organic extracts were combined, dried (Na$_2$SO$_4$), and the solvent was evaporated under reduced pressure to yield the title compound.

MS: mass calcd. for C$_{22}$H$_{21}$FN$_4$O, 376.17; m/z found, 378.4 [M+H]$^+$.

EXAMPLE 12

(S)-Hydroxy-phenyl-acetic acid 2,5-dioxo-pyrrolidin-1-yl ester

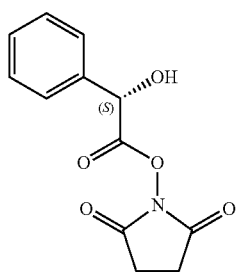

To a solution of (S)-(+)-mandelic acid (0.50 g, 3.3 mmol) and N-hydroxy succinimide (0.38 g, 3.3 mmol) in EtOAc (10 mL) was added 1,3-dicyclohexylcarbodiimide (0.67 g, 3.3 mmol) in EtOAC (5 mL) drop wise. The resulting solution was let stir for 4 h and then filtered. The filtrate was concentrated under reduced pressure and the resulting residue was used in the next step without further purification.

EXAMPLE 13

N,N-Diethyl-2(S)-hydroxy-2-phenyl-acetamide

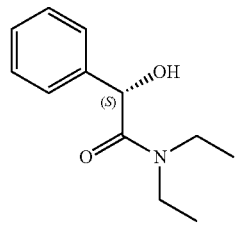

To a solution of the hydroxy-phenyl-acetic acid 2,5-dioxo-pyrrolidin-1-yl ester (0.70 g, 2.8 mmol) in THF/H$_2$O (10 mL, 1:1) was added diethylamine (25% in H$_2$O, 0.58 mL, 5.6 mmol). After stirring for 16 h, the reaction solvent was evaporated under reduced pressure. The resulting residue was diluted with H$_2$O and extracted with EtOAc (3×50 mL). The organic extracts were combined, dried (Na$_2$SO$_4$), and the solvent was evaporated under reduced pressure to yield the title compound.

MS: mass calcd. for C$_{12}$H$_{17}$NO$_2$, 207.13; m/z found, 208.2 [M+H]$^+$.

EXAMPLE 14

(S)-Methanesulfonic acid diethylcarbamoyl-phenyl-methyl ester

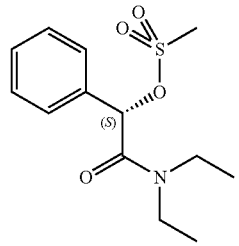

To a solution of N,N-diethyl-2-hydroxy-2-phenyl-acetamide (0.18 g, 0.9 mmol), Et$_3$N (0.36 mL, 2.6 mmol), and CH$_2$Cl$_2$ (10 mL) at 0° C. was added methane sulfonyl chloride (0.08 mL, 1.0 mmol). After stirring for an hour, the reaction mixture was quenched with H$_2$O (5 mL) and extracted with CH$_2$Cl$_2$ (3×25 mL). The orgranic extracts were combined, dried (Na$_2$SO$_4$), and the solvent was evaporated under reduced pressure. Chromatography of the resulting residue (SiO$_2$: EtOAc:Hex) yielded the title compound.

MS: mass calcd. for C$_{13}$H$_{19}$NO$_4$S, 285.10; m/z found, 286.2 [M+H]$^+$.

EXAMPLE 15

(−)-N-{4-[4-(Diethylcarbamoyl-phenyl-methyl)-piperazin-1-yl]-3-fluoro-phenyl}-2-pyridin-3-yl-benzamide

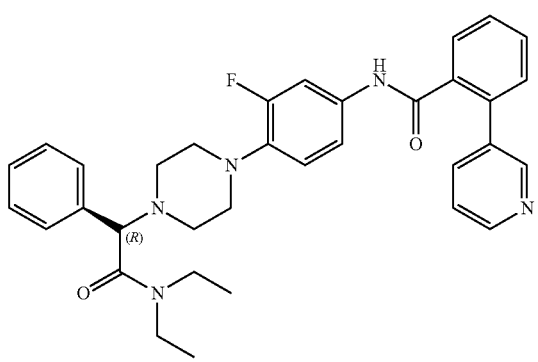

A solution of N-(3-fluoro-4-piperazin-1-yl-phenyl)-2-pyridin-3-yl-benzamide (0.16 g, 0.4 mmol) and methanesulfonic acid diethylcarbamoyl-phenyl-methyl ester (0.06 g, 0.2 mmol) in DMF (1 mL) was heated at 50° C. After five hours, the reaction mixture was quenched with H$_2$O (5 mL) and extracted with EtOAc (4×10 mL). The organic extracts were combined, dried (Na$_2$SO$_4$), and the solvent was evaporated under reduced pressure. Chromatography of the residue (SiO$_2$: NH$_3$ (MeOH):CH$_2$Cl$_2$) yielded the title compound.

MS (ESI): mass calcd. for C$_{34}$H$_{36}$FN$_5$O$_2$, 565.29; m/z found, 566.4 [M+H]$^+$.

$^1$H-NMR(400 MHz, CDCl$_3$) δ ppm: 8.64 (s, 1H), 8.52 (d, J=4.8 Hz, 1H), 7.93 (s, 1H), 7.77 (s, 1H), 7.71 (d, J=7.6 Hz, 1H), 7.55-7.47 (m, 4H), 7.40-7.30 (m, 6H), 6.85-6.84 (m, 1H), 6.78-6.75 (m, 1H), 3.42-3.12 (m, 9H), 2.88-2.84 (m, 4H), 1.08-1.06 (t, 7.1 Hz, 3H), 1.02-0.98 (t, J=7.0 Hz, 3H).

EXAMPLE 16

2-bromo-N-ethyl-2-phenyl-acetamide

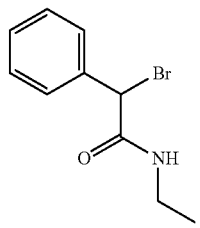

The title compound was prepared according to the process as described in Example 2 above, substituting ethylamine for diethylamine.

EXAMPLE 17

N-Ethyl-2-[4-(2-fluoro-4-nitro-phenyl)-piperazin-1-yl]-2-phenyl-acetamide (Compound (B))

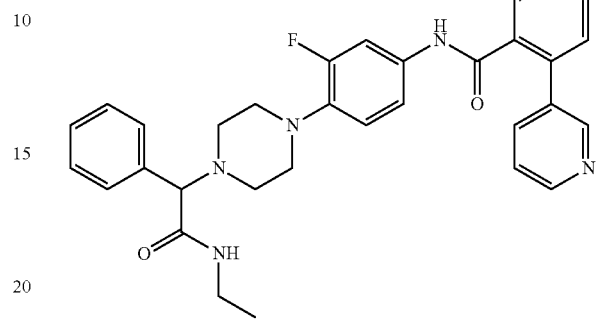

A mixture of [2-[4-(4-amino-2-fluoro-phenyl)-piperazin-1-yl]-N-ethyl-2-phenyl-acetamide (320 mg, 0.90 mmol), 2-(3'-pyridyl) benzoic acid (200 mg, 0.99 mmol) and HATU (375 mg, 0.99 mmol) in DMF (10 mL) was treated with DIPEA (170 µL, 0.99 mmol) and let stir at room temperature for 6 h. The reaction mixture was quenched with H$_2$O and extracted with EtOAc. The organic layer was separated and washed (sat'd NaHCO$_3$, brine), dried (Na$_2$SO$_4$), filtered and concentrated to yield a semi solid, which was purified by PTLC (5% 2M NH$_3$/MeOH in CH$_2$Cl$_2$) to yield the title compound as a brown foam.

MS (ESI): mass calcd. for C$_{32}$H$_{32}$FN$_5$O$_2$, 537.64; m/z found, 538.5 [M+H]$^+$.

$^1$H NMR (CDCl$_3$): 8.74-8.73 (m, 1H), 8.62-8.60 (m, 1H), 7.80-7.76 (m, 2H), 7.60-7.57 (m, 1H), 7.54-7.50 (m, 1H), 7.46-7.43 (m, 1H), 7.33-7.29 (m, 6H), 7.18-7.15 (m, 1H), 7.09-7.00 (m, 2H), 6.91 (s, 1H), 6.84-6.77 (m, 1H), 3.87 (s, 1H), 3.35-3.32 (m, 2H), 3.05-3.04 (m, 4H), 2.61-2.58 (m, 4H), 1.16 (t, J=7.2, 3H).

EXAMPLE 18 & 19

(+) and (−)-N-Ethyl-2-[4-(2-fluoro-4-nitro-phenyl)-piperazin-1-yl]-2-phenyl-acetamide

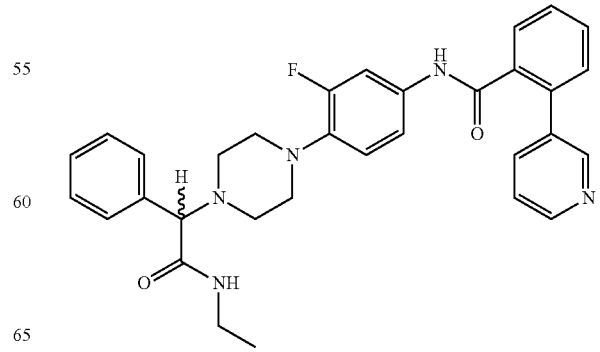

Racemic N-{4-[4-(ethylcarbamoyl-phenyl-methyl)-piperazin-1-yl]-3-fluoro-phenyl}-2-pyridin-3-yl-benzamide (100 mg, 0.18 mmol) was separated by SFC to give the (+) enantiomer of the title compound as a tan solid and the (−) enantiomer of the title compound as a tan solid.

SFC conditions: column: AD-H column (Chiral Technologies) 4.6×250mm for analytical; 21×250mm for prep with the following parameters: flow rate: 2ml/min for analytical; 37.5 ml/min for prep; Mobile Phase A: 0.1% triethyl amine in MeOH; Mobile Phase B: $CO_2$; isocratic 20° % A/80% B; pressure: 100 bar; and temp: 25° C.

(+) Enantiomer: (Retention Time: 21.13 min)
Optical Rotation $[\alpha]^{20}{}_D$+16.98° (c 0.69, MeOH)
MS (ESI): mass calcd. for $C_{32}H_{32}FN_5O_2$, 537.64; m/z found, 538.4 $[M+H]^+$.
$^1$H NMR ($CDCl_3$): 7.77 (d, J=7.7, 1H), 7.74-7.71 (m, 1H), 7.57-7.54 (m, 1H), 7.50-7.46 (m, 2H), 7.39 (d, J=7.5, 1H), 7.32-7.28 (m, 6H), 7.18 (dd, J=13.8, 2.2, 1H), 7.08-7.05 (m, 1H), 6.89-6.86 (m, 1H), 6.78 (t, J=9.0, 1H), 3.85 (s, 1H), 3.35-3.28 (m, 2H), 3.04-3.02 (m, 4H), 2.72-2.68 (m, 2H), 2.58-2.54 (m, 4H), 1.16-1.08 (m, 3H).

(−) Enantiomer: (Retention Time: 28.34 min)
Optical rotation $[\alpha]^{20}{}_D$−18.40° (c 0.72, MeOH)
MS (ESI): mass calcd. for $C_{32}H_{32}FN_5O_2$, 537.64; m/z found, 538.4 $[M+H]^+$.
$^1$H NMR ($CDCl_3$): 8.67 (s, 1H), 8.57-8.56 (m, 1H), 7.79-7.77 (m, 1H), 7.75-7.73 (m, 1H), 7.58-7.55 (m, 1H), 7.51-7.48 (m, 1H), 7.41 (d, J=7.0, 1H), 7.33-7.28 (m, 5H), 7.18 (dd, J=2.3, 13.8, 1H), 7.08-7.05 (m, 1H), 6.87-6.85 (m, 1H), 6.78 (t, J=9.0, 1H), 3.86 (s, 1H), 3.35-3.29 (m, 2H), 3.04-3.02 (m, 4H), 2.83-2.78 (m, 2H), 2.58-2.54 (m, 4H), 1.21-1.15 (m, 3H).

EXAMPLE 20

Biphenyl-2-carboxylic acid (3-fluoro-4-piperazin-1-yl-phenyl)-amide

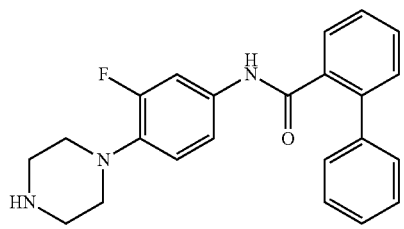

To a solution of 4-(4-Amino-2-fluoro-phenyl)-piperazine-1-carboxylic acid tert-butyl ester (0.50 g, 1.7 mmol) and biphenyl-2-carboxylic acid (0.38 g, 1.9 mmol) in $CH_2Cl_2$ (30 mL) was added 1-hydroxybenzotriazole hydrate (0.27 g, 2.0 mmol), and 1-[3-(dimethylamino)propyl]-3-ethylcarbodiimide hydrochloride (0.38 g, 2.0 mmol). After stirring at room temperature for 18 h, the reaction was diluted with 1 N NaOH (50 mL) and extracted with $CH_2Cl_2$ (3×50 mL). The organic extracts were combined, dried ($Na_2SO_4$), and concentrated. Chromatography of the resulting residue ($SiO_2$: EtOAc/hexanes) yielded 4-{4-[(biphenyl-2-carbonyl)-amino]-2-fluoro-phenyl}-piperazine-1-carboxylic acid tert-butyl ester, which was further dissolved in MeOH (20 mL) and 4N HCl in dioxanes. After stirring for 5 h, the reaction mixture was concentrated down, neutralized with 1N NaOH, and extracted with EtOAc (3×75mL). The orgranic extracts were combined, dried ($Na_2SO_4$), and the solvent was evaporated under reduced pressure to yield the title compound.

MS (ESI): mass calcd. for $C_{23}H_{22}FN_3O$, 375.17; m/z found, 376.3 $[M+H]^+$.

EXAMPLE 21

Biphenyl-2-carboxylic acid {4-[4-(diethylcarbamoyl-phenyl-methyl)-piperazin-1-yl]-3-fluoro-phenyl}-amide (Compound (C))

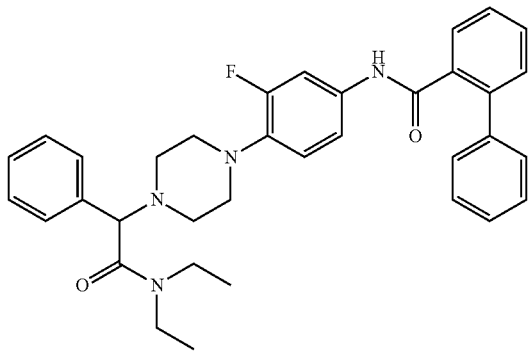

A solution of biphenyl-2-carboxylic acid (3-fluoro-4-piperazin-1-yl-phenyl)-amide (0.030 g, 0.08 mmol), 2-bromo-N,N-diethyl-2-phenyl-acetamide (0.025 g, 0.09 mmol), and $Na_2CO_3$ (0.013 g, 0.1 mmol) in DMF (2 mL) was stirred at room temperature. After 18 h, the reaction mixture was diluted with EtOAc (25 mL) and washed with $H_2O$ (3×15 mL). The organic layers were combined, dried ($Na_2SO_4$), and concentrated. Chromatography of the resulting residue ($SiO_2$: 2 M $NH_3$ in MeOH/$CH_2Cl_2$) yielded the title compound.

MS (ESI) mass calcd. for $C_{35}H_{37}FN_4O_2$, 564.29; m/z found, 565.4 $[M+H]^+$.

$^1$H NMR ($CDCl_3$): 8.01 (s, 1H), 7.87 (d, J=7.6, 1H), 7.53-7.48 (m, 1H), 7.47-7.31 (m, 10H), 7.09-7.07 (m, 1H), 6.84 (s, 1H), 6.76-6.72 (m, 1H), 6.55-6.53 (m, 1H), 4.23 (bs, 1H), 3.47-3.39 (m, 2H), 3.29-3.25 (m, 2H), 3.05 (bs, 4H), 2.66 (bs, 4H), 1.09-1.03 (m, 6H).

EXAMPLE 22

N-{4-[4-(Diethylcarbamoyl-phenyl-methyl)-piperazin-1-yl]-3-fluoro-phenyl}-2-pyridin-3-yl-benzamide citrate salt

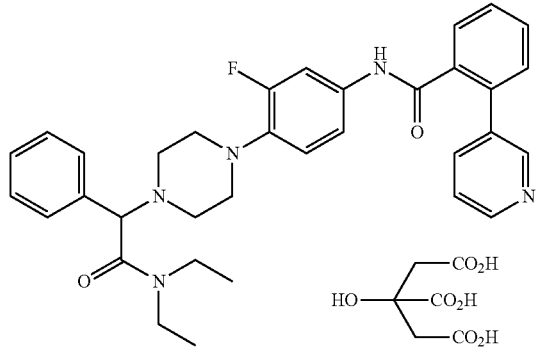

To a 100 mL flask charged with absolute ethanol (25 mL) was added N-{4-[4-(diethylcarbamoyl-phenyl-methyl)-piperazin-1-yl]-3-fluoro-phenyl}-2-pyridin-3-yl-benzamide (495.4 mg, 0.87 mmol). Mild heating with a heat gun, sonication and addition of $CH_2Cl_2$ (4 mL) resulted in a homogeneous solution. Citric acid (171.1 mg) was then added in one portion and the resulting mixture was stirred until homogenous, then allowed to stand for 1 h. The solvents were removed with the rotary evaporator to yield an off-white foam. The foam was stirred over a 2:1 mixture of diethyl ether and ethyl acetate (60 mL) for 6 h. The resulting solids were collected on filter paper, washed with diethyl ether and dried under vacuum to yield the title compound as an off-white powder.

MS (ESI): mass calcd. for $C_{40}H_{44}FN_5O_9$, 757.80; m/z found, 566.2 [M+H]$^+$(free Base).

EXAMPLE 23

N-{4-[4-(Diethylcarbamoyl-phenyl-methyl)-piperazin-1-yl]-3-fluoro-phenyl}-2-pyridin-3-yl-benzamide maleate salt

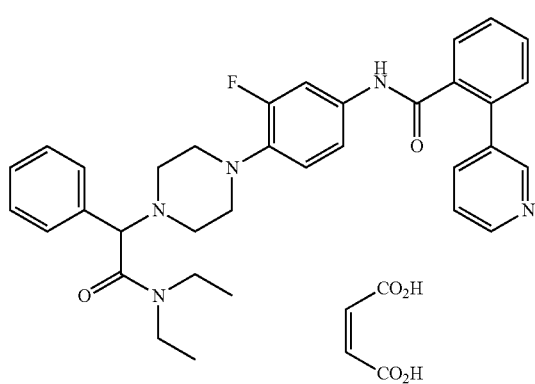

In a 100 mL flask charged with absolute ethanol (20 mL) ethanol was added N-{4-[4-(diethylcarbamoyl-phenyl-methyl)-piperazin-1-yl]-3-fluoro-phenyl}-2-pyridin-3-yl-benzamide (273.7 mg, 0.48 mmol). Sonication and addition of $CH_2Cl_2$ (4 mL) yielded a homogeneous solution. Maleic acid (62.6 mg) was then added in one portion and the resulting mixture stirred for 3 h. The solvents were removed with the rotary evaporator to yield an off-white foam. The foam was dried under vacuum to yield the title compound as an off-white foam.

MS (ESI): mass calcd. for $C_{38}H_{40}FN_5O_6$, 681.75; m/z found, 566.2 [M+H]$^+$(free Base).

EXAMPLE BIO-1

Neuropeptide $Y_2$ Radioligand Binding Assay

Radioligand binding assays for the human and rat/mouse $Y_2$ receptor were performed as described in Bonaventure, P., D. Nepomuceno, C. Mazur, B. Lord, D. A. Rudolph, J. A. Jablonowski, N. I. Carruthers and T. W. Lovenberg, *J Pharmacol Exp Ther.* 2004, 308, 1130.

KAN-Ts endogenously expressing $Y_2$ receptors were used, for the rat and mouse $Y_2$ receptor, membranes from rat or mouse hippocampus were prepared. Membranes were incubated with [$^{125}$I]PYY (80 pM) in the presence or absence of test compound for 1 h at rt. The reaction was stopped by filtration through GF/C filter plates pre-soaked in 0.3% polyethylenimine and subsequently washed with Tris-HCl, 50 mM, 5 mM EDTA buffer. Plates were dried for 1 h in a 55° C. oven, scintillation fluid was added and the radioactivity was counted in a Packard TopCount. Specific binding to the NPY receptor subtypes was determined by radioactivity that was bound in the presence of 1 μM NPY.

Apparent $K_i$ values were calculated as $K=IC_{50}/(1+C/K_D)$, where C is concentration of the radioligand and $pK_i=-\log K_i$. Data presented below are expressed as mean±S.E.M.

Receptor binding assays in KAN-Ts cells endogenously expressing human $Y_2$ receptors demonstrated that the compound of formula (A) competes with high affinity against specific [$^{125}$I]PYY receptor binding sites (as shown in Table 1, below). At concentrations up to 10 the compound of formula (A) failed to compete for significant amounts of specific [$^{125}$I]PYY receptor binding sites in HEK-293 cells expressing the $Y_5$ receptor subtype.

EXAMPLE BIO2

[$^{35}$S] GTPγS Binding Assay in KAN-Ts Cells

[$^{35}$S] GTPγS binding assay in KAN-Ts cells was performed as described in Bonaventure, P., D. Nepomuceno, C. Mazur, B. Lord, D. A. Rudolph, J. A. Jablonowski, N. I. Carruthers and T. W. Lovenberg, *J Pharmacol Exp Ther.* 2004, 308, 1130.

Assay mixtures (150 were preincubated with compounds for 30 minutes at ambient temperature. Then, 50 μl of [$^{35}$S] GTPγS in assay buffer was added to a final concentration of 200 pM and the assay mixtures were incubated for 1 hour at ambient temperature. Reactions were terminated by rapid filtration thought GF/C filters. Filters were washed twice with ice cold 50 mM Tris-HCl, pH 7.4 containing 10 mM $MgCl_2$. Basal [$^{35}$S]GTPγS was measured in the absence of compounds. In initial experiments, nonspecific binding was measured in the presence of 100 μM GTPgS. This nonspecific binding never exceeded 10% of basal binding and was thus not subtracted from experimental data. Stimulation of [$^{35}$S] GTPγS was determined as percentage over basal and was calculated as one hundred times the difference between stimulated and basal binding (in cpm). Agonist concentration-response curves for increases in [$^{35}$S]GTPγS binding and antagonist inhibition curves for inhibition of PYY (300 nM)-stimulated [$^{35}$S]GTPγS binding were analyzed by non-linear regression using GraphPad Prism software (GraphPad Software Inc., San Diego Calif.). $EC_{50}$ (concentration of compound at which 50% of its own maximal stimulation is obtained) and $IC_{50}$ (concentration of its own maximal inhibition of PYY-stimulated [$^{35}$S]GTPγS binding is obtained) were derived from the curves. $IC_{50}$ values were corrected as follows: corrected $IC_{50}$ ($IC_{50}$ corr)=$IC_{50}$ /(1+[PYY]/$EC_{50}$ (PYY)) and $pIC_{50}$corr=$-\log IC_{50}$corr. Data are expressed as mean±S.E.M.

The antagonistic properties of the compound of formula (A) were evaluated in a [$^{35}$S]GTPγS binding assay in KAN-Ts cells endogenously expressing human $Y_2$ receptors. The compound of formula (A), by itself, did not affect [$^{35}$S]GTPγS binding up to 10 μM. The compound of formula (A) was further examined for its ability to inhibit PYY (300 nM)-stimulated [$^{35}$S]GTPγS binding to membranes of $Y_2$-KAN-Ts cells. The compound of formula (A) exhibited antagonistic properties and inhibited the PYY-stimulated [$^{35}$S]GTγS binding to basal level with a pIC$_{50}$ corr of 10.3, as listed in Table 1 below.

EXAMPLE BIO3

Ca2+ Mobilization Assays in KAN-Ts Cells

The assay was performed using the fluorimetric imaging plate reader (FLIPR) format as described in Dautzenberg, F. M., *Biochemical Pharmacology* 2005, 69, 1493.

KAN-Ts cells stably expressing chimeric G proteins were seeded at a density of 100,000 cells into poly-d-lysine coated 384-well blackwall, clear-bottom microtiter plates (Corning, N.Y.). One day later, the medium was removed and 50 µl loading medium DMEM high glucose, without serum, supplemented with 10 mM HEPES-acid, 0.1% BSA, 5 mM probenecid and 2 µM Fluo-3AM was added. Cells were loaded for 1 h at 37° C., washed twice with 50 µl assay buffer (5 mM HEPES-acid, 140 mM NaCl, 1 mM MgCl$_2$, 5 mM KCl, 10 mM glucose) and then 30 µl assay buffer was added. Cells were further pre-incubated at room temperature before adding agonists or agonists plus antagonists in 20 µl assay buffer and then measured on a T-channel fluorometric imaging plate reader (FLIPR, Molecular Devices, Sunnyvale, Calif.).

Antagonistic potency values were converted to apparent pK$_B$ values using a modified Cheng-Prusoff correction. Apparent pK$_B$=−log IC$_{50}$/1+[conc agonist/EC$_{50}$]. Data below are expressed as mean±S.E.M.

The in vitro antagonistic properties of the compound of formula (A) were confirmed using Ca$^{2+}$ measurement. The compound of formula (A) inhibited PYY stimulated Ca2+ increase with a pKb=8.57, as listed in Table 1 below.

Table 1 below summarizes the biological activity for representative compounds of the present invention, as measured in assays as described in Examples BIO1-BIO3 above. In the Tables which follow herein, the designation (+)-Cmpd (A) denotes the (+) enantiomer of the compound of formula (A), (−)-Cmpd (A) denotes (−) enantiomer of the compound of formula (A), (+)-Cmpd (B) denotes the (+) enantiomer of the compound of formula (B) and (−)-Cmpd (B) denotes the (−) enantiomer of the compound of formula (B).

EXAMPLE 4

MTP Receptor Binding Assay

MTP activity was measured using an assay similar to one described by J. R. Wetterau and D. B. Zilversmit in *Chemistry and Physics of Lipids* (1985) 38, 205-222.

In order to prepare the donor and acceptor vesicles, the appropriate lipids in chloroform were put into a glass test tube and dried under a stream of nitrogen. A buffer containing 15 mM Tris-HCl (pH 7.5), 1 mM ethylenediamine tetra-acetic acid, 40 mM NaCl, 0.02% NaN$_3$ (assay buffer) was added to the dried lipid. The mixture was vortexed briefly and the lipids were then allowed to hydrate for 20 minutes on ice. Vesicles were then prepared by bath sonication (using a Branson 2200 device) at room temperature for at most 15 minutes. Butylated hydroxytoluene was included in all vesicle preparations at a concentration of 0.1%. The lipid transfer assay mixture contained donor vesicles (40 nmole phosphatidylcholine, 7.5 mole % cardiolipin and 0.25 mole % glycerol tri[1-$^{14}$C]-oleate), acceptor vesicles (240 nmol phosphatidylcholine) and 5 mg bovine serum albumin in a total volume of 675 µl in a 1.5 ml microcentrifuge tube. Test compound was added dissolved in dimethylsulfoxide (0.13% final concentration). After 5 minutes of pre-incubation at 37° C., the reaction was started by the addition of MTP in 100 µl of a dialysis buffer. The reaction was stopped by the addition of 400 µl diethylaminoalkyl (DEAE)-52 cellulose (Sephadex) pre-equilibrated in 15 mM Tris-HCl (pH 7.5), 1 mM ethylenediamine tetra-acetic acid and 0.02% NaN$_3$ (1:1 volume/volume). The mixture was agitated for 4 minutes and centrifuged for 2 minutes at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

Representative compounds of the present invention were measured for binding against the MTP receptor, as described above, with results as listed in Table 2 below.

TABLE 1

In vitro affinity and potency against the NPY Y$_2$ receptor

| | Assay | Cmpd (A) | (−)-Cmpd (A) | (+)-Cmpd (A) | Cmpd (C) |
|---|---|---|---|---|---|
| hY$_2$ pKi | [$^{125}$I]PYY, KANT-S cells | 8.26 ± 0.04 | 8.50 | 8.10 | 8.12 ± 0.16 |
| rY$_2$ pKi | [$^{125}$I]PYY, hippocampus | 8.34 ± 0.06 | 7.92 | 8.00 | 7.60 |
| mY$_2$ pKi | [$^{125}$I]PYY, hippocampus | 8.35 ± 0.17 | 8.10 | | |
| hY$_2$ pIC$_{50}$corr | [$^{35}$S]GTγS KANT-S cells | 10.30 ± 0.06 | | | |
| hY$_2$ pK$_B$ | FLIPR KANT-S cells | 8.57 ± 0.42 | 9.10 | 9.40 | 8.2 |

| | Assay | Cmpd (B) | (−)-Cmpd (B) | (+)-Cmpd (B) |
|---|---|---|---|---|
| hY$_2$ pKi | [$^{125}$I]PYY, KANT-S cells | 7.49 ± 0.17 | 7.40 ± 0.21 | 6.64 ± 0.20 |
| hY$_2$ pK$_B$ | FLIPR KANT-S cells | 7.3 | | |

TABLE 2

MTP Assay Results

| Compound | pIC$_{50}$ |
|---|---|
| Cmpd (A) | 6.1 |
| (−)-Cmpd (A) | 5.2 |
| (+)-Cmpd (A) | 6.5 |
| Cmpd (B) | 6.6 |
| (−)-Cmpd (B) | 6.4 |
| (+)-Cmpd (B) | 5.4 |
| Cmpd (C) | 7.3 |

EXAMPLE BIO5

CEREP

The selectivity of the compound of formula (A) was further evaluated in a large variety of ion-channels, transporters and receptor-binding assays including the Y$_1$ receptor subtype. These assays were performed by CEREP (Celles L'Evescault, France; www.cere.com<http//www.cerea.com>). Selectivity vs the Y$_5$ receptor subtype was evaluated as described in Bonaventure, P., D. Nepomuceno, C. Mazur, B. Lord, D. A. Rudolph, J. A. Jablonowski, N. I. Carruthers and T. W. Lovenberg, *J Pharmacol Exp Ther.* 2004, 308, 1130.

The compound of formula (A) was assayed by binding in a panel of 50 receptors, ion channels and transporters assays (CEREP) including adenosine (A$_1$, A$_2$A, A$_3$), adrenergic ($\alpha_1$, $\alpha_2$, $\beta_1$), angiotensin (AT$_1$), dopamine (D$_1$, D$_2$), bradykinin (B$_2$), cholecystokinin (CCKA), galanin (GAL$_2$), melatonin ML$_1$), muscarinic (M$_1$, M$_2$, M$_3$), neurotensin (NT$_S$), neurokinin (NK$_2$, NK$_3$), NPY (Y$_1$, Y$_2$) opiate (m, k, d), serotonin (5-HT$_{1A}$, 5-HT$_{1B}$, 5-HT$_{2A}$, 5-HT$_3$, 5-HT$_{5A}$, 5-HT$_6$, 5-HT$_7$), somatostatin, vasopressin (V1a), norepinephrine transporter, dopamine transporter and ion channels (sodium, calcium, potassium and chloride). The compound of formula (A), at concentrations up to 1 µM exhibited inhibition of less than 50% against each of these receptors, except against the NPY Y$_2$ receptor, where % inhibition at 1 µM was measured at 100%. Against the NPY Y$_1$ receptor, the compound of formula (A) exhibited a % inihibition at 1 µM of 10%.

EXAMPLE BIO6

Pharmacokinetic, Blood-Brain Barrier Penetration and Ex vivo Receptor Occupancy Studies in Rats The pharmacokinetic, blood-brain barrier penetration and ex vivo receptor occupancy studies were performed as described in Bonaventure, P., D. Nepomuceno, C. Mazur, B. Lord, D. A. Rudolph, J. A. Jablonowski, N. I. Carruthers and T. W. Lovenberg, *J Pharmacol Exp Ther.* 2004, 308, 1130.

The compound of formula (A) was formulated in 20% hydroxypropylbetacyclodextrine. Subcutaneous (SC), oral (PO) or intravenous (IV) dosing was followed by blood sampling via cardiac puncture over a time course. Blood samples consisted of 250 µl samples taken from the heart using a 23-gauge needle into 1.5 ml micro-centrifuge tubes. Brains were removed from the animals and bisected down the mid-sagittal plane. One hemisphere was frozen on dry ice for ex vivo receptor binding autoradiography and the other was homogenized for LC/MS-MS analysis.

All blood samples were deproteinized by 1:4 dilution of the sample with acetonitrile with vigorous mixing. These samples were incubated for 5 minutes, and then centrifuged at 14,000 rpm in a micro-centrifuge for 4 minutes. The supernatant was recovered into auto-sampler vials and diluted 1:1 with sterile water. Samples were analyzed by LC-MS/MS. A Vydac SP C18 2.1×50 mm analytical column was used for separation.

Ex vivo receptor binding autoradiography was performed on brain sections. Twenty-micron-thick coronal sections at the level of the hypothalamic regions were collected and incubated for 10 min with 100 pM [$^{125}$I]PYY in Krebs-Ringer phosphate buffer (KRP) at pH 7.4 supplemented with 0.1% BSA, 0.05% bacitracin, and 1 µM BIBP-3226 for Y$_1$ receptor occlusion. The sections were not washed prior to incubation and were incubated 10 minutes to avoid dissociation. Non-specific binding was determined using adjacent sections incubated in the presence of 1 µM unlabelled hNPY. At the end of the incubation, sections were washed 4 times (4 minutes each) in ice cold buffer, dipped in deionized water and rapidly dried under a stream of cold air. Sections were exposed to a Fujifilm Imaging Plate (BAS-MS2025) for 12 hours. The Phosphor Imaging Plate was scanned using a Fuji Bio-Imaging Analyzer System (BAS-5000). The digitized computer images generated by the scanner were visualized and quantified using ImageGauge V3.12 software (Fujifilm).

Figure 2:
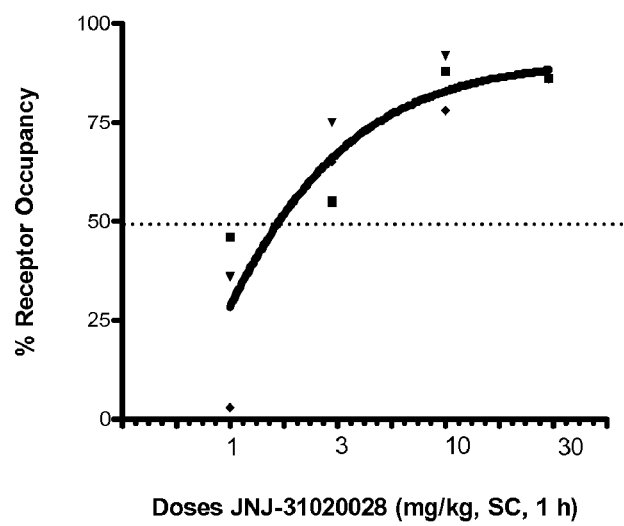
FIG. 2 illustrates dose dependency on ex vivo $Y_2$ receptor occupancy in rat hippocampus for the compound of formula (A) after SC administration at t=60 min.

The ex vivo receptor occupancy study (SC 10 mg/kg) showed that the compound of formula (A) occupied Y$_2$ receptor binding sites in rat hippocampus. The maximal receptor binding site occupancy was found ~1 hours, as shown in FIG. 1. Y$_2$ ex vivo receptor occupancy after subcutaneous administration of the compound of formula (A) was time dependant and parallel the plasma concentration, as shown in FIG. 1. Ex vivo receptor occupancy was also found to be dose dependant (as shown in FIG. 2, ED$_{50}$=2 mg/kg). Maximal ex vivo receptor occupancy (close to 100%) was observed at 10 mg/kg SC.

In additional studies, Compound B, after SC administration (10 mg/kg), ~40% Y$_2$ receptor occupancy in the rat brain. By contrast, Compound C, after SC administration (10 mg/kg), did not show any significant level of Y$_2$ receptor occupancy in rat brain.

Oral, subcutaneous and intravenous pharmacokinetic parameters of the compound of formula (A) were determined in rats and are listed in Table 2 below.

TABLE 2

Pharmacokinetic parameters for the Compound of Formula (A) after oral (10 mg/kg), subcutaneous (10 mg/kg) and intravenous administration in the rat

| | PO | SC | IV |
|---|---|---|---|
| Tmax (hr) | 0.500 | 0.500 | |
| Cmax (µmol/L) | 0.414 | 4.346 | |
| C$_0$ (µmol/L) | | | 5.330 |
| AUC$_{INF}$ (hr × µmol/L) | 0.444 | 7.913 | 0.708 |
| T$_{1/2}$ (hr) | 0.530 | 0.834 | 0.290 |
| % F | 6% | >100% | |
| V$_z$ (L/kg) | | | 1.066 |
| V$_{SS}$ (L/kg) | | | 0.730 |
| Cl (mL/min/kg) | | | 42.280 |

EXAMPLE BIO7

Pharmacokinetic Study in Dogs

Male Beagle Canines 11-15 kilograms in body weight were used. Three animals received a bolus oral dose of the compound via an oral gavage at a dose of 5 mg/kg. Three animals received a bolus intravenous dose of the compound at a dose of 1 mg/kg in the right cephalic vein. Blood sampling of the cephalic or jugular veins followed dosing over a time course. Blood samples consisted of 4-5 mL samples taken from the vein into heparinized blood collection tubes containing Li Heparin. These blood samples were then centrifuged. The plasma was retained and kept frozen in a −40° C. freezer until processed for analysis. The time course for sampling was as follows: 0.25, 0.5, 1, 2, 4, 8, and 24 hours for oral administration and 0.08, 0.25, 0.5, 1, 2, 4, 8, and 24 hours for intravenous administration. These samples were analyzed by LC-MS/MS. The LC-MS/MS data was analyzed using a non-compartmental model with the software package WinNonlin Version 4.0.1 (Pharsight, Palo Alto, Calif.). All figures plasma level versus time figures were created using GraphPad Prism 4 (San Diego, Calif.).

Figure 3:
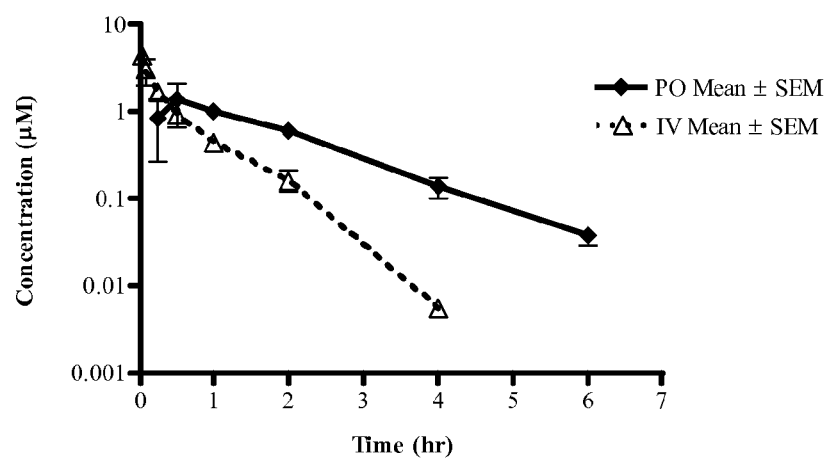
FIG. 3 illustrates pharmacokinetics of the compound of formula (A) following oral (5 mg/kg) and intravenous (0.5 mg/kg) administration in the male beagle dogs.

The compound of formula (A) was formulated in 20% hydroxypropyl-β-cyclodextrine. Oral and intravenous pharmacokinetic parameters for the compound of formula (A) were determined in male Beagles with results as shown in FIG. 3 and Table 3 below.

TABLE 3

Pharmacokinetic parameters for the compound of formula (A) after oral (5 mg/kg), and intravenous (1 mg/kg) administration in the dog

| | PO | | IV |
|---|---|---|---|
| Tmax (hr) | 0.83 | | |
| Cmax (µmol/L0 | 1.55 | | |
| Lambda z *1/hr) | 0.71 | Lambda z *1/hr) | 1.47 |
| $AUC_{INF}$ (hr × µmol/L) | 2.79 | $AUC_{INF}$ (hr × µmol/L) | 1.89 |
| $AUC_{LAST}$ (hr × µmol/L0 | 2.73 | $AUC_{LAST}$ (hr × µmol/L0 | .89 |
| $MRT_{INF}$ (hr) | 1.72 | $MRT_{INF}$ (hr) | 0.61 |
| $T_{1/2}$ (hr) | 0.99 | $T_{1/2}$ (hr) | 0.47 |
| | | C0 (µmol/L) | 6.24 |
| | | $V_z$ (L/kg) | 0.64 |
| | | $V_{SS}$ (L/kg) | 0.57 |
| | | Cl (mL/min/kg) | 15.80 |

EXAMPLE BIO8

Ethanol Locomotor Activity Assay

C57bl6/j mice readily self-administer ethanol and these mice are sensitive to the stimulant effects of alcohol. NPY immunoreactivity is reduced in these mice. In addition, mice lacking NPY drink more ethanol than wild type mice; whereas, mice over-expressing NPY have reduced preference for ethanol. Experiments were designed to test the hypothesis that selective blockade of Y2 receptors by the compound of formula (A) decreases ethanol stimulant effects presumable by enhancing NPY function in the brain.

Experiment A: Blockade of Ethanol-Induced Hyperactivity in c57bl6/i Mice

Locomotor activity was measured with a Hamilton Kinder motor monitor infrared beam apparatus equipped with a SmartFrame cage rack throughout which basic movements were recorded. Experiments assessed the effects of the compound of formula (A) on ethanol-induced hyperactivity in 8-10-week old c57bl6/j mice and were conducted using a between subject design. Vehicle (10 ml/kg, i.p.) or the compound of formula (A) (10 mg/kg, i.p.) was administered 15 min prior to the beginning of the session. Thereafter, animals received an acute injection of either vehicle (10 ml/kg, i.p.) or ethanol (1 g/kg, i.p), then they were immediately placed in the apparatus and locomotor activity was evaluated for 15 min. Data were analyzed with two-way repeated ANOVA using Graph Pad.

Experiment B: Blockade of Amphetamine-Induced Hyperactivity in c57bl6/j Mice

To the extent that ethanol-induced hyperactivity is mediated, at least partially, by the dopaminergic system, additional experiments were designed to evaluate whether the compound of formula (A) attenuates the hyperactivity induced by amphetamine, an indirect dopamine agonist.

Locomotor activity was measured with a Hamilton Kinder motor monitor infrared beam apparatus equipped with a SmartFrame cage rack throughout which basic movements were recorded. These experiments were conducted using a between subject design. Sessions started when 8-10-week old c57bl6/j mice were located in the test cages and they lasted for 180 min. Amphetamine (3 mg/kg, s.c.) was administered 60 min after the beginning of the session. The compound of formula (A) (1,3,10 mg/kg, i.p.) or vehicle was administered 15 min prior to amphetamine and locomotor activity was measured for an additional 120 min. The average of basic movements recorded for 60 min after amphetamine was calculated for each animal. Data were analyzed with one-way analysis of variance (ANOVA) using Graph Pad.

Figure 4:
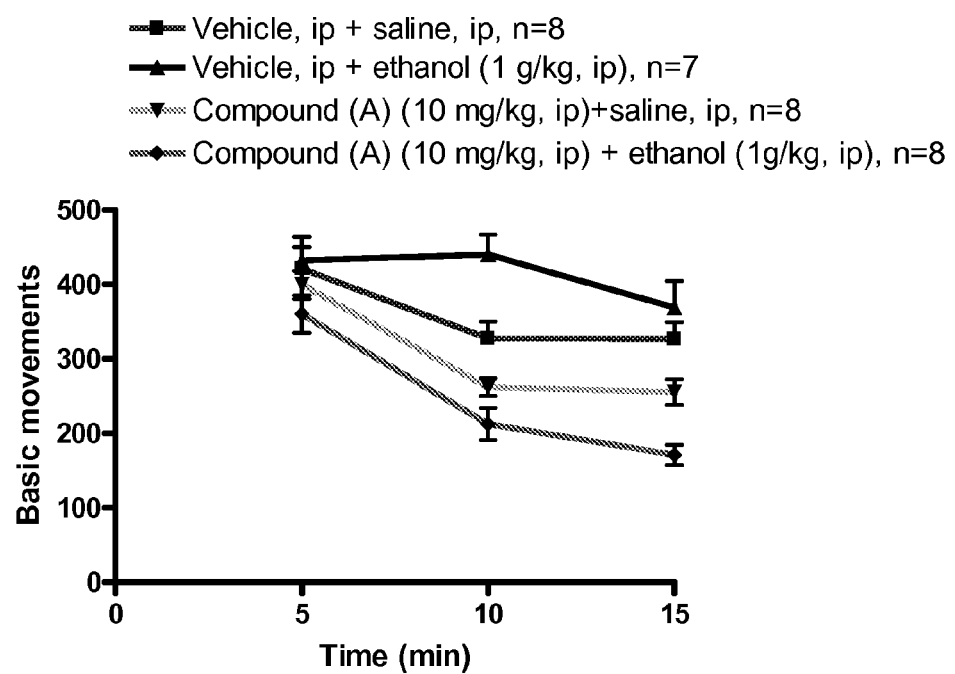
FIG. 4 illustrates the effects of the compound of formula (A) (dosing at 10 mg/kg, i.p.) on ethanol (1g/kg, i.p.)-induced hyperactivity.

Results Experiment A:

Two-way repeated measure ANOVA indicated there was a main treatment effect [F (3, 27)=33.6, p<0.05)]. Post-hoc analysis conducted with Bonferroni's test indicated that ethanol significantly increased locomotor activity compared to vehicle. The compound of formula (A) (10 mg/kg) significantly reduced ethanol hyperactivity and did not change locomotor activity by itself, as shown in FIG. 4 below. These results indicate that the compound of formula (A) selectively reduces ethanol hyperactivity. To the extent that the psychostimulant effects of ethanol are related to its rewarding effects, these results suggest that the compound of formula (A) may be effective in reducing abuse-related effects of ethanol (i.e. self-administration).

Figure 5:
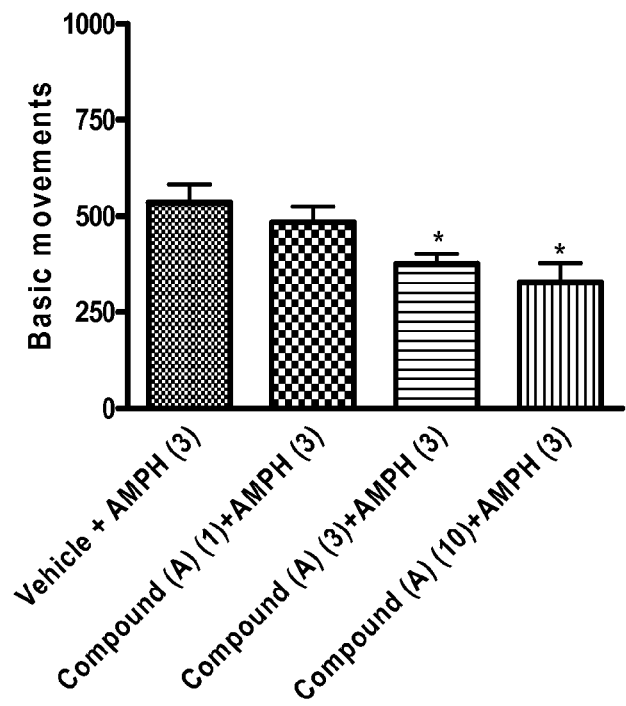
FIG. 5 illustrates the effect of the compound of formula (A) (dosing at 1, 3 and 10 mg/kg, i.p., n=5-7/group) on amphetamine (3 mg/kg, s.c.)-induced hyperactivity.

Results Experiment B:

One-way ANOVA analysis indicated that there was a main treatment effect [F(3, 21)=5.08, p<0.05)]. Post-hoc analysis conducted with Dunnett's test indicated that the compound of formula (A) (at 3 and 10 mg/kg dosing) blocked amphetamine-induced hyperactivity, as shown in FIG. 5 below. These results suggest that the effects of the compound of formula (A) on ethanol-induced hyperactivity are likely mediated by the dopaminergic system.

EXAMPLE FORMULATION 1

As a specific embodiment of an oral composition, 100 mg of the compound of formula (A) or the compound of formula (B) is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (A)

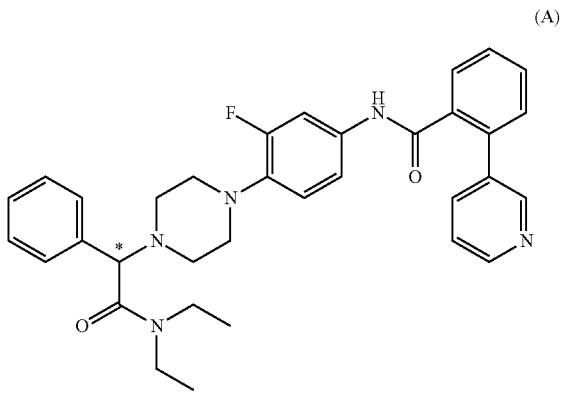

(A)

or an enantiomer or pharmaceutically acceptable salt thereof.

2. A compound of formula (A-S)

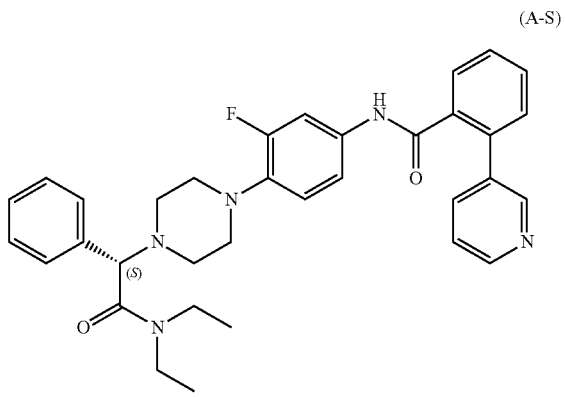

or a pharmaceutically acceptable salt thereof.
3. A compound of formula (A-R)

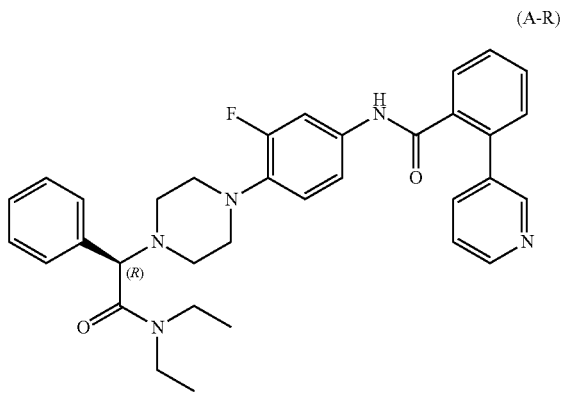

or a pharmaceutically acceptable salt thereof.
4. A pharmaceutical composition comprising a pharmaceutically acceptable carrier and a compound of claim 1.
5. A pharmaceutical composition made by mixing a compound of claim 1 and a pharmaceutically acceptable carrier.
6. A process for making a pharmaceutical composition comprising mixing a compound of claim 1 and a pharmaceutically acceptable carrier.
7. A compound of formula (B)

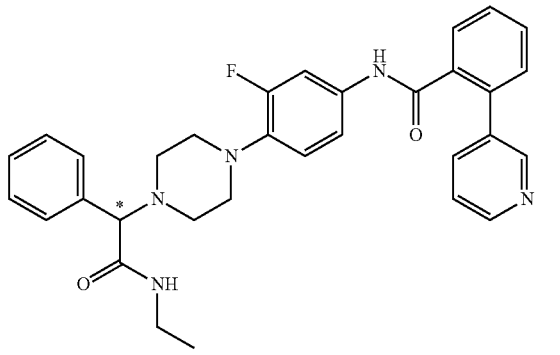

or an enantiomer or pharmaceutically acceptable salt thereof.

8. A compound of formula (B-S)

(B-S)

or a pharmaceutically acceptable salt thereof.
9. A compound of formula (B-R)

(B-R)

or a pharmaceutically acceptable salt thereof.
10. A pharmaceutical composition comprising a pharmaceutically acceptable carrier and a compound of claim 7.
11. A pharmaceutical composition made by mixing a compound of claim 7 and a pharmaceutically acceptable carrier.
12. A process for making a pharmaceutical composition comprising mixing a compound of claim 7 and a pharmaceutically acceptable carrier.
13. A compound as in claim 1, wherein the compound is a pharmaceutically acceptable salt of the compound of formula (A)

(A)

14. A compound as in claim 13, wherein the pharmaceutically acceptable salt of the compound of formula (A) is selected from the group consisting of a citrate salt of the compound of formula (A), a maleate salt of the compound of formula (A) and a bis-HCl salt of the compound of formula (A).

15. A compound as in claim 13, wherein the pharmaceutically acceptable salt of the compound of formula (A) is a bis-HCl salt of the compound of formula (A).

* * * * *